US008808300B2

(12) United States Patent
Leyden et al.

(10) Patent No.: US 8,808,300 B2
(45) Date of Patent: Aug. 19, 2014

(54) GUIDE ASSEMBLY FOR USE IN A MEDICAL PROCEDURE

(75) Inventors: Matthew V. Leyden, St. Paul, MN (US); Aaron J. Bisek, Elk River, MN (US); David A. Hawkes, Winona Lake, IN (US); Marc E. Ruhling, Goshen, IN (US); Jeffrey B. Waffensmith, North Oaks, MN (US); Matthew S. Wallace, Fort Wayne, IN (US)

(73) Assignee: Biomet C.V., Gibraltar (GI)

( * ) Notice: Subject to any disclaimer, the term of this patent is extended or adjusted under 35 U.S.C. 154(b) by 1354 days.

(21) Appl. No.: 11/904,520

(22) Filed: Sep. 27, 2007

(65) Prior Publication Data
US 2009/0088767 A1 Apr. 2, 2009

(51) Int. Cl.
*A61B 17/68* (2006.01)
*A61F 2/46* (2006.01)

(52) U.S. Cl.
USPC .......................................... 606/96; 606/86 B

(58) Field of Classification Search
USPC .............. 606/86 A, 86 R, 96–104, 281, 86 B
See application file for complete search history.

(56) References Cited

U.S. PATENT DOCUMENTS

| | | | |
|---|---|---|---|
| 2,526,959 A | 10/1950 | Lorenzo | |
| 3,554,193 A | 1/1971 | Konstantinou et al. | |
| 4,341,206 A * | 7/1982 | Perrett et al. | 606/80 |
| 4,438,762 A | 3/1984 | Kyle | |
| 4,465,065 A * | 8/1984 | Gotfried | 606/65 |
| 5,047,034 A * | 9/1991 | Sohngen | 606/87 |
| 5,324,292 A | 6/1994 | Meyers | |
| 5,409,493 A * | 4/1995 | Greenberg | 606/96 |
| 5,429,641 A * | 7/1995 | Gotfried | 606/67 |
| 5,743,916 A * | 4/1998 | Greenberg et al. | 606/102 |
| 5,746,743 A * | 5/1998 | Greenberg | 606/96 |
| 5,985,390 A * | 11/1999 | DeGrand | 428/36.6 |
| 6,110,178 A * | 8/2000 | Zech et al. | 606/96 |

(Continued)

FOREIGN PATENT DOCUMENTS

WO WO 2005/084559 9/2006
WO WO 2005/084560 9/2006

OTHER PUBLICATIONS

Colored DePuy Orthopaedics' brochure entitled "Captured Hip Screw System Surgical Technique"; Published at least as early as Sep. 26, 2007; Nineteen (19) pages.

(Continued)

*Primary Examiner* — Matthew Lawson
(74) *Attorney, Agent, or Firm* — Harness, Dickey

(57) ABSTRACT

An assembly includes a guide component having (i) a base defining a first passageway, and (ii) a handle attached to the base, the base including a first coupling component. The assembly further includes a first sheath defining a second passageway, the first sheath including a second coupling component configured to cooperate with the first coupling component to couple the first sheath to the base. The first passageway is aligned with the second passageway when the first sheath is coupled to the base. The assembly further includes a stop structure defining a central passage, the stop structure including an external surface having a plurality of keyways defined therein. The first sheath includes a key member configured to be selectively received in any one of the plurality of keyways. The stop structure is fixed in relation to the first sheath when the key member is positioned in any one of the plurality of keyways.

23 Claims, 37 Drawing Sheets

(56) References Cited

U.S. PATENT DOCUMENTS

| | | | |
|---|---|---|---|
| 6,866,667 B2* | 3/2005 | Wood et al. | 606/96 |
| 6,916,323 B2* | 7/2005 | Kitchens | 606/86 R |
| 6,926,720 B2* | 8/2005 | Castaneda | 606/98 |
| 7,056,322 B2 | 6/2006 | Davison et al. | |
| 7,153,309 B2* | 12/2006 | Huebner et al. | 606/96 |
| 7,270,666 B2* | 9/2007 | Lombardo et al. | 606/308 |
| 7,316,687 B2* | 1/2008 | Aikins et al. | 606/70 |
| 2003/0040748 A1* | 2/2003 | Aikins et al. | 606/70 |
| 2003/0040752 A1* | 2/2003 | Kitchens | 606/86 |
| 2005/0049594 A1* | 3/2005 | Wack et al. | 606/69 |
| 2005/0085824 A1* | 4/2005 | Castaneda | 606/98 |
| 2005/0085825 A1* | 4/2005 | Castaneda | 606/102 |
| 2006/0095044 A1* | 5/2006 | Grady et al. | 606/96 |
| 2007/0162011 A1 | 7/2007 | Leyden et al. | |
| 2007/0173843 A1* | 7/2007 | Matityahu | 606/69 |
| 2008/0027458 A1* | 1/2008 | Aikins et al. | 606/96 |

OTHER PUBLICATIONS wisdomking.com web site: *Plastic 180° Pocket Goniometer—121005*; http://www.wisdomking.com/product55238.html. Downloaded from website on Sep. 9, 2007 (2 pages).

Amazon.com website: "*goniometer*", http://www.amazon.com/exec/obidos/search-handle-url/index=blended&field-keywords=go . . . Downloaded from website on Sep. 9, 2007 (4 pages).

* cited by examiner

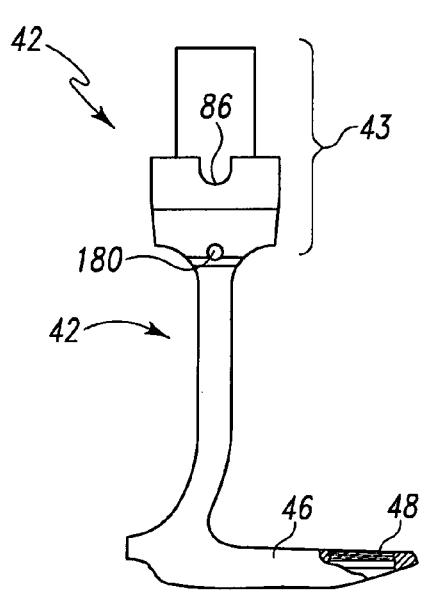
Fig. 9
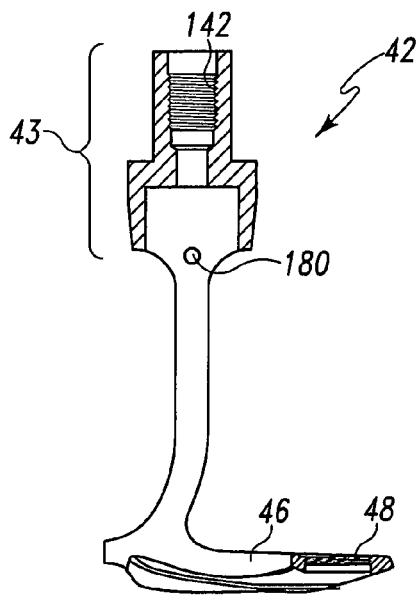
Fig. 10
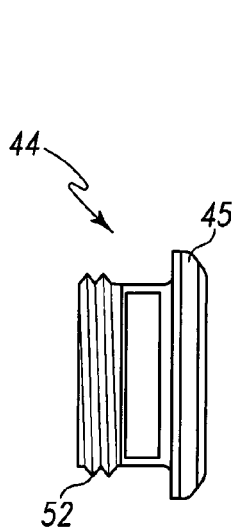
Fig. 11
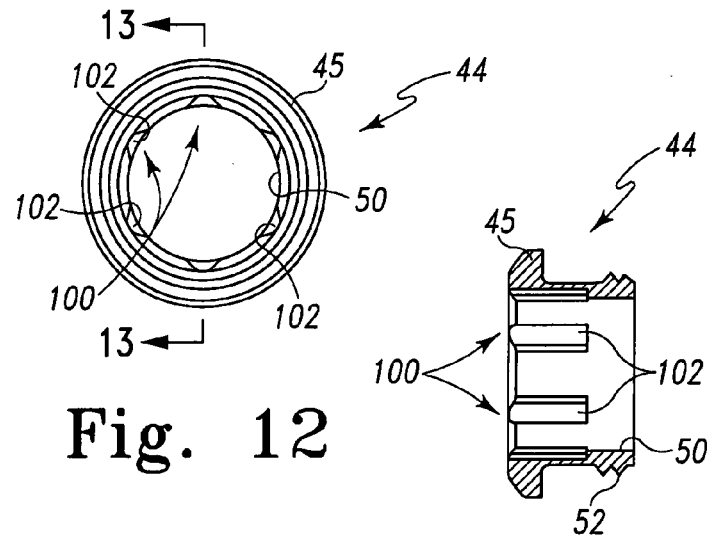
Fig. 12
Fig. 13

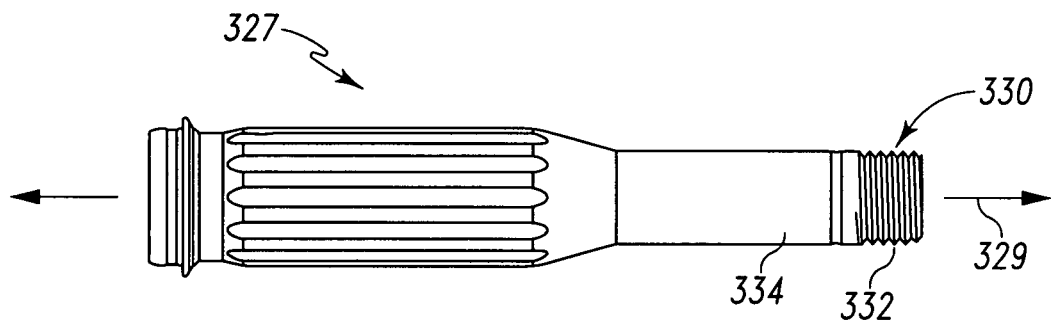
Fig. 44
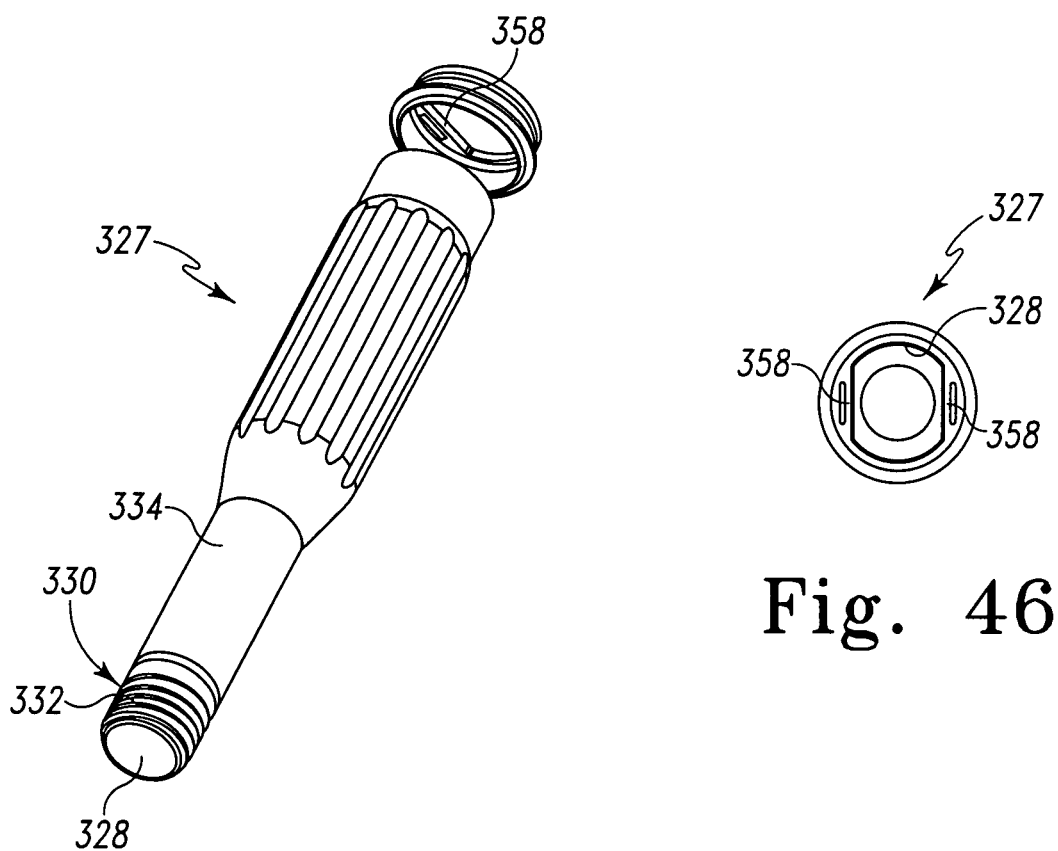
Fig. 45
Fig. 46

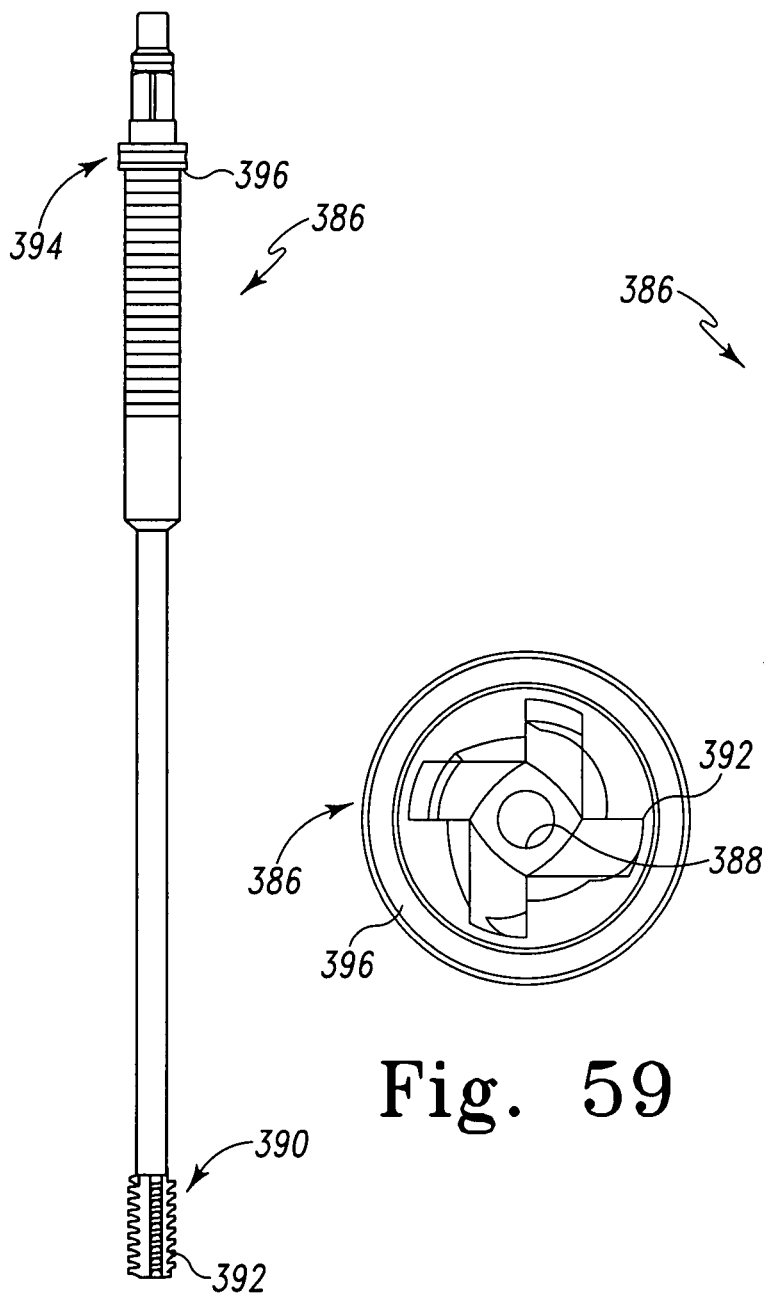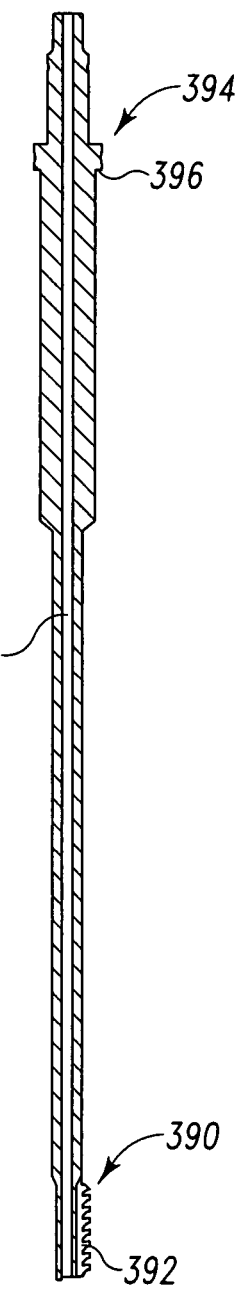
Fig. 57      Fig. 59      Fig. 58

GUIDE ASSEMBLY FOR USE IN A MEDICAL PROCEDURE

CROSS REFERENCE TO RELATED APPLICATIONS

Cross reference is made to copending (i) U.S. patent application Ser. No. 11/904,414, entitled "Plate Holder Assembly having Movable Guide Component" by Richard Kyle, Jeffrey Waffensmith, Matthew Leyden, Tim Bachman, Matthew Wallace, and Marc Ruhling, (ii) U.S. patent application Ser. No. 11/904,504, entitled "Plate Holder Assembly having Bone Plate Seating Confirmation Arrangement" by Matthew Leyden, Jeffrey Waffensmith, Tim Bachman, Matthew Wallace, Marc Ruhling, Anthony J. Metzinger, and Charles Christie, (iii) U.S. patent application Ser. No. 11/904,476, entitled "Plate Holder and Bone Plate Arrangement" by Matthew Leyden, Jeffrey Waffensmith, Matthew Wallace, and Marc Ruhling, and (iv) U.S. patent application Ser. No. 11/904,399, entitled "Apparatus for Measuring an Angle of a Guide Wire Relative to a Bone" by Stuart R. Grant, Anthony J. Metzinger, David A. Hawkes, and Andrew H. Berthusen, which are assigned to the same assignee as the present invention, and which are filed concurrently herewith. The disclosures of the four above-identified patent applications are herein totally incorporated by reference in their entirety.

BACKGROUND

The present disclosure relates generally to instrumentation used in a medical procedure, and more particularly, relates to a guide assembly used in the reduction of a hip fracture.

A procedure regularly performed by orthopaedic surgeons is the reduction of a hip fracture caused by trauma. The site of this type of fracture typically exists at the proximal portion of the femur below the head. In order to reduce a fracture of this type, an elongated lag screw is threadingly advanced into the shaft, neck, and head of the femur, and secured to a bone plate. Cortical screws are used to secure the bone plate to the femur distal to the fracture site. Tightening of the lag screw compresses the bone fragments together and facilitates healing of the femur. Many devices have been designed for this type of reduction including the devices disclosed in U.S. Pat. Nos. 4,438,762, 3,554,193, and 2,526,959, the disclosures of which are incorporated herein by reference in their entirety.

It is a goal of designers of medical instrumentation to design apparatus used in hip fracture reduction procedures that facilitate implantation a bone plate assembly in a relatively less invasive manner. It is a further goal of such designers to design apparatus used in hip fracture reduction procedures that are relatively less complex and easy to use.

What is needed therefore is an assembly used in hip fracture reduction procedures that facilitates implantation a bone plate assembly in a relatively less invasive manner. What is also needed is an assembly used in hip fracture reduction procedures that is relatively less complex and easy to use.

SUMMARY

In accordance with one embodiment of the disclosure, there is provided an assembly that includes a guide component including (i) a base defining a first passageway, and (ii) a handle attached to the base, the base including a first coupling component. The assembly further includes a first sheath defining a second passageway, the first sheath including a second coupling component configured to cooperate with the first coupling component to couple the first sheath to the base. The first passageway is aligned with the second passageway when the first sheath is coupled to the base.

Pursuant to another embodiment of the disclosure, there is provided an assembly that includes a sheath defining a first central passage and having a key member. The assembly further includes a stop structure defining a second central passage, the stop structure including an external surface having a plurality of keyways defined therein. The key member is configured to be selectively received in any one of the plurality of keyways. The stop structure is fixed in relation to the sheath when the key member is positioned in any one of the plurality of keyways. The first central passage is aligned with the second central passage when the key member is positioned in any one of the plurality of keyways.

In accordance with yet another embodiment of the disclosure, there is provided an assembly that includes a guide component including (i) a base defining a first passageway, and (ii) a handle attached to the base, the base including a first coupling component. The assembly further includes a first sheath defining a second passageway, the first sheath including a second coupling component configured to cooperate with the first coupling component to couple the first sheath to the base, and the first passageway being aligned with the second passageway when the first sheath is coupled to the base. In addition, the assembly includes a second sheath defining a third passageway, the second sheath being positionable within the second passageway of the first sheath. The assembly also includes a guide wire positionable within the third passageway of the second sheath. Furthermore, the assembly includes a stop structure defining a central passage, the stop structure including an external surface having a plurality of keyways defined therein, wherein (i) the first sheath includes a key member configured to be selectively received in any one of the plurality of keyways, and (ii) the stop structure is fixed in relation to the first sheath when the key member is positioned in any one of the plurality of keyways. Also, the assembly includes a drill configured to be received within the central passage of the stop structure when the stop structure is received within the second passageway of the first sheath, wherein (i) the drill includes a first distal portion having a first cutting surface, and a first proximal portion having a first shoulder, and (ii) the first shoulder contacts the stop structure to prevent further advancement of the drill through the central passage of the stop structure when the drill is received within the central passage of the stop structure.

BRIEF DESCRIPTION OF THE DRAWINGS

FIG. 9 is a side elevational view of the plate holder of the instrument assembly of FIG. 5;

FIG. 10 is a cross sectional view of the plate holder of the instrument assembly of FIG. 5;

FIG. 11 is a side elevational view of the coupling component of the instrument assembly of FIG. 5;

FIG. 12 is a top elevational view of the coupling component of the instrument assembly of FIG. 5;

FIG. 13 is a cross sectional view of the coupling component taken along the line 13-13 of FIG. 12;

FIG. 44 is a side elevational view of a sheath that is used to prepare a fastener cavity in a femur of a patient in a minimally invasive manner according to the present disclosure;

FIG. 45 is an exploded, perspective view of the sheath of FIG. 44;

FIG. 46 is an end elevational view of the sheath of FIG. 44;

FIG. 57 is a side elevational view of a tap (with its handle removed) that is used to prepare a fastener cavity in a femur of a patient in a minimally invasive manner according to the present disclosure;

FIG. 58 is a cross sectional view of the tap of FIG. 57;

FIG. 59 is an end elevational view of the tap of FIG. 57;

DESCRIPTION OF THE PREFERRED EMBODIMENTS

Figure 1:
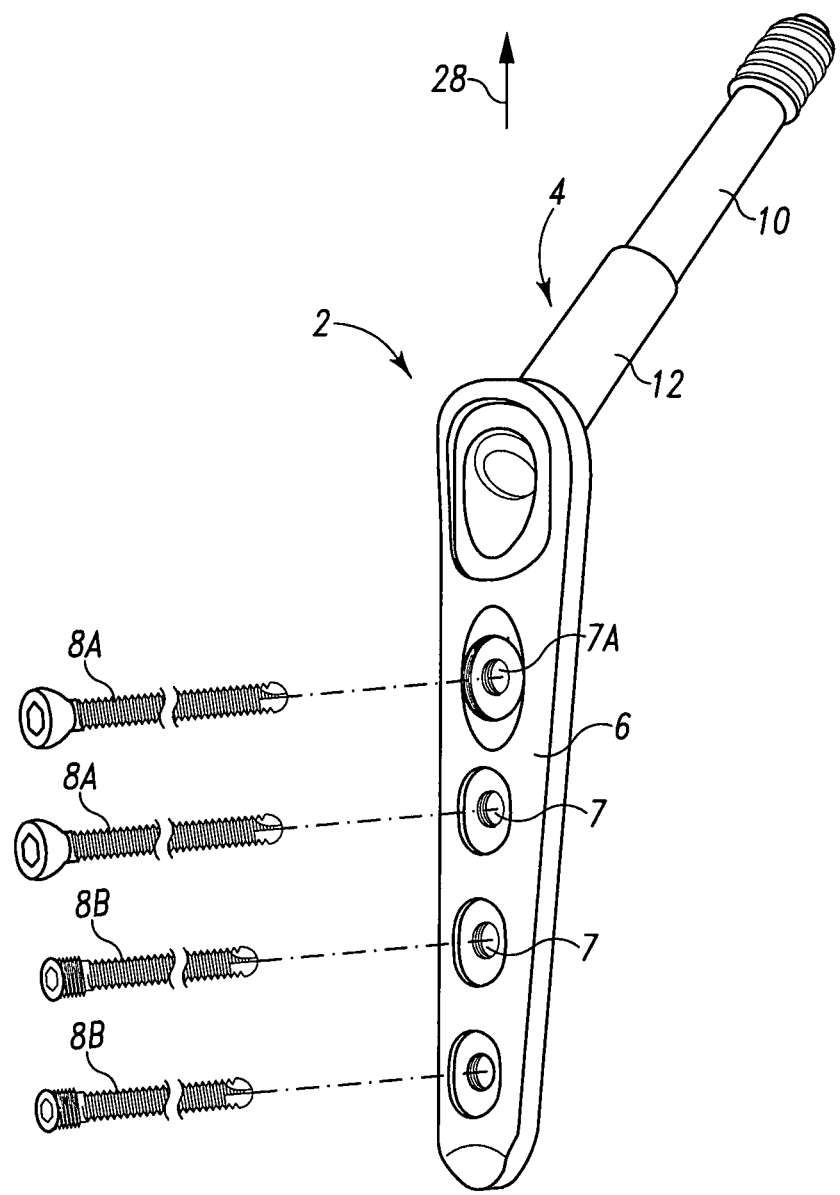
FIG. 1 is a perspective view of an implant assembly which is implanted in a minimally invasive manner according to the present disclosure.
Figure 2A:
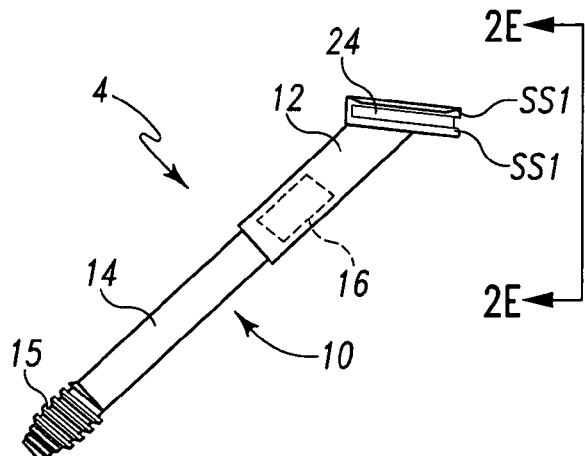
FIG. 2A is a side elevational view of the lag screw assembly of the implant assembly of FIG. 1.
Figure 2B:
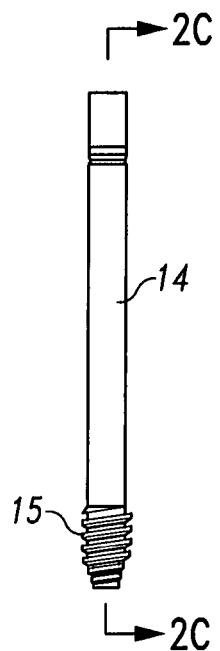
FIG. 2B is a side elevational view of the lag screw component of the lag screw assembly of FIG. 2A.
Figure 2D:
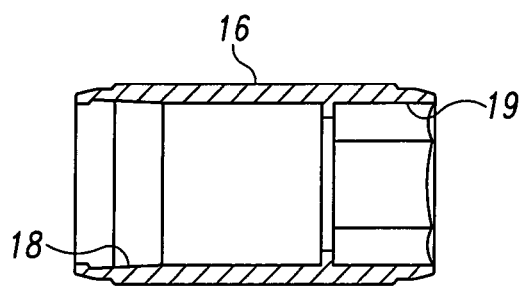
FIG. 2D is a cross sectional view of the sleeve of the lag screw assembly of FIG. 2A.
Figure 2E:
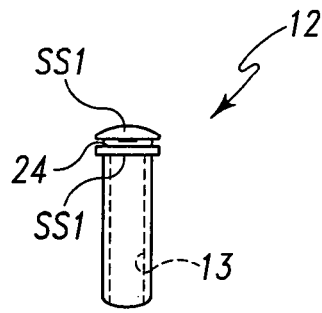
FIG. 2E is a side elevational view of the fastener guide taken along the line 2E-2E of FIG. 2A.
Figure 2C:
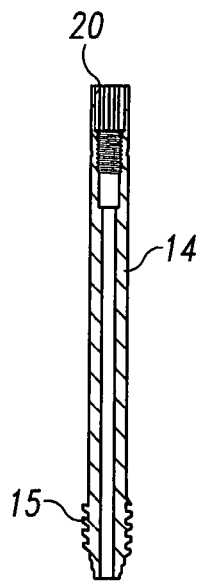
FIG. 2C is a cross sectional view of the lag screw component taken along the line 2C-2C of FIG. 2B.

While the assembly described herein is susceptible to various modifications and alternative forms, specific embodiments thereof have been shown by way of example in the drawings and will herein be described in detail. It should be understood, however, that there is no intent to limit the assembly to the particular forms disclosed, but on the contrary, the intention is to cover all modifications, equivalents, and alternatives falling within the spirit and scope of the invention as defined by the appended claims.

Instrumentation and Implant Components

Described below are instrumentation and implant components that facilitate reduction of a hip fracture in a minimally invasive manner. As shown in FIGS. 1, 2A-2E, and 3A-3D, the implant components include an implant assembly 2 that includes a lag screw assembly 4, a bone plate 6, and a plurality of bone screws 8A, 8B. The bone screws 8A include two non-locking cortical bone screws, while the bone screws 8B include two locking cortical bone screws. Alternatively, other combinations of locking screws 8A and non-locking screws 8B may be used with the bone plate 6. Further, instead of using a combination of locking and non-locking screws, all locking screws 8B may used with the bone plate 6, or alternatively all non-locking screws 8A may be used with the bone plate 6.

Figure 3A:
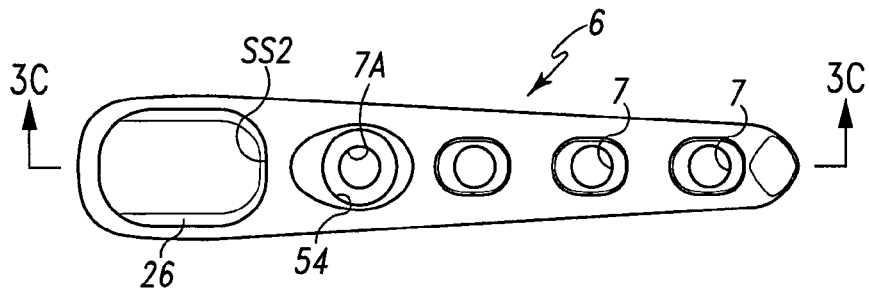
FIG. 3A is a top elevational view of the bone plate of the implant assembly of FIG. 1.
Figure 3B:
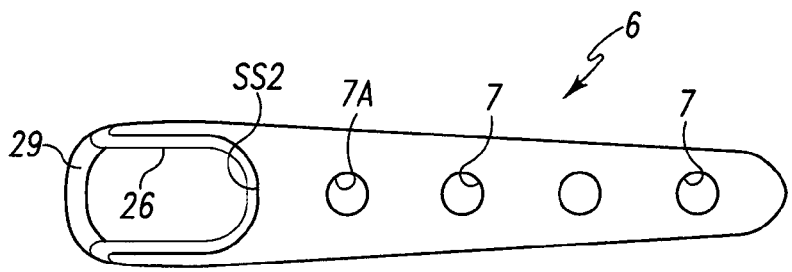
FIG. 3B is a bottom elevational view of the bone plate of the implant assembly of FIG. 1.
Figure 3C:
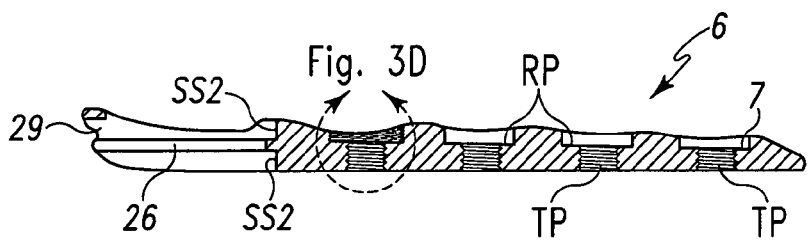
FIG. 3C is a cross sectional view of the bone plate taken along the line 3C-3C of FIG. 3A.
Figure 3D:
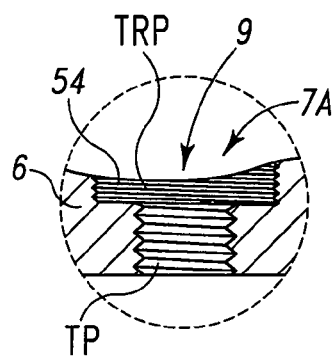
FIG. 3D is an enlarged, fragmentary, cross sectional view of the bone plate showing the portion of FIG. 3C that is encircled and identified as FIG. 3D.

The bone plate 6 has defined therein a plurality of fastener openings 7, 7A configured to receive the bone screws 8A, 8B. Each of the fastener openings 7 include a recess portion RP and a threaded portion TP that are aligned with each other as shown in FIG. 3C. The fastener opening 7A includes a threaded recess portion TRP and a threaded portion TP that are aligned with each other as shown in FIG. 3D. The threaded recess portion TRP defines a set of internal threads 54. The structure of the bone plate 6 that defines the threaded recess portion TRP creates a coupling component 9.

The lag screw assembly 4 includes a lag screw 10 and a fastener guide or barrel 12. The fastener guide 12 defines a passage 13 in which the lag screw 10 is partially positioned. The lag screw 10 includes a lag screw component 14 and a sleeve 16 that are rotatably attached together. The lag screw component 14 has defined therein a plurality of threads 15. The sleeve 16 is configured to slide axially within the passage 13 of the fastener guide 12, but is prevented from being able to rotate in relation to the fastener guide 12 by mating structure (not shown) of the sleeve 16 and fastener guide 12. The sleeve 16 has defined therein a passage 18 that defines a hexagonal shaped recess 19. The lag screw component 14 is freely rotatable in relation to the sleeve 16. However, when a keying mechanism (not shown) is positioned within the recess 19 of the sleeve 16 and a hexagonal-shaped recess 20 of the lag screw component 14, the sleeve 16 and the lag screw component 14 are rotationally or angularly locked together. In other words, rotation of the sleeve 16 causes rotation of the lag screw component 14. Thus, when the keying mechanism is positioned within the recess 19 and the recess 20, the lag screw component 14 is rotationally or angularly locked in relation to the fastener guide 12 since the sleeve 16 is prevented rotating in relation to the fastener guide 12 as discussed above. However, the lag screw component 14 is able to slide axially in relation to the passage 13 of the fastener guide 12.

Alternatively, the sleeve 16 may be permanently fixed in relation to the lag screw component 14 so that, after assembly of these components, rotation of the sleeve 16 causes rotation of the lag screw component 14. An alternative lag screw assembly that may be utilized in the lag screw assembly 4 is the lag screw assembly disclosed in U.S. Patent Application Publication No. US2007/0162011, having a U.S. application Ser. No. 11/303,833, the disclosure of which is herein incorporated by reference in its entirety.

The bone plate 6 cooperates with the lag screw assembly 4 to assume the configuration shown in FIG. 1. In particular, the fastener guide 12 defines a channel 24. The channel 24 is preferably U-shaped. The bone plate 6 defines an access opening 29 through which the fastener guide 12 may advance. The bone plate 6 includes a projection 26. The projection 26 is preferably U-shaped. The projection 26 of the bone plate 6 is configured to be received within the channel 24 of fastener guide 12. In order to mate the bone plate 6 with the lag screw assembly 4, the bone plate 6 is advanced in the direction indicated by arrow 28 (see FIG. 1) so that the fastener guide 12 passes through the access opening 29 of the bone plate whereby the projection 26 of the bone plate is received within the channel 24 of the fastener guide. Continued advancement of the bone plate 6 in relation to the fastener guide 12 in the direction of arrow 28 results in a seating surface SS1 of the fastener guide 12 contacting a seating surface SS2 of the bone plate 6. When seating surface SS1 is positioned in contact with the seating surface SS2, the bone plate 6 and the fastener guide 12 are in an assembled state.

Figure 4:
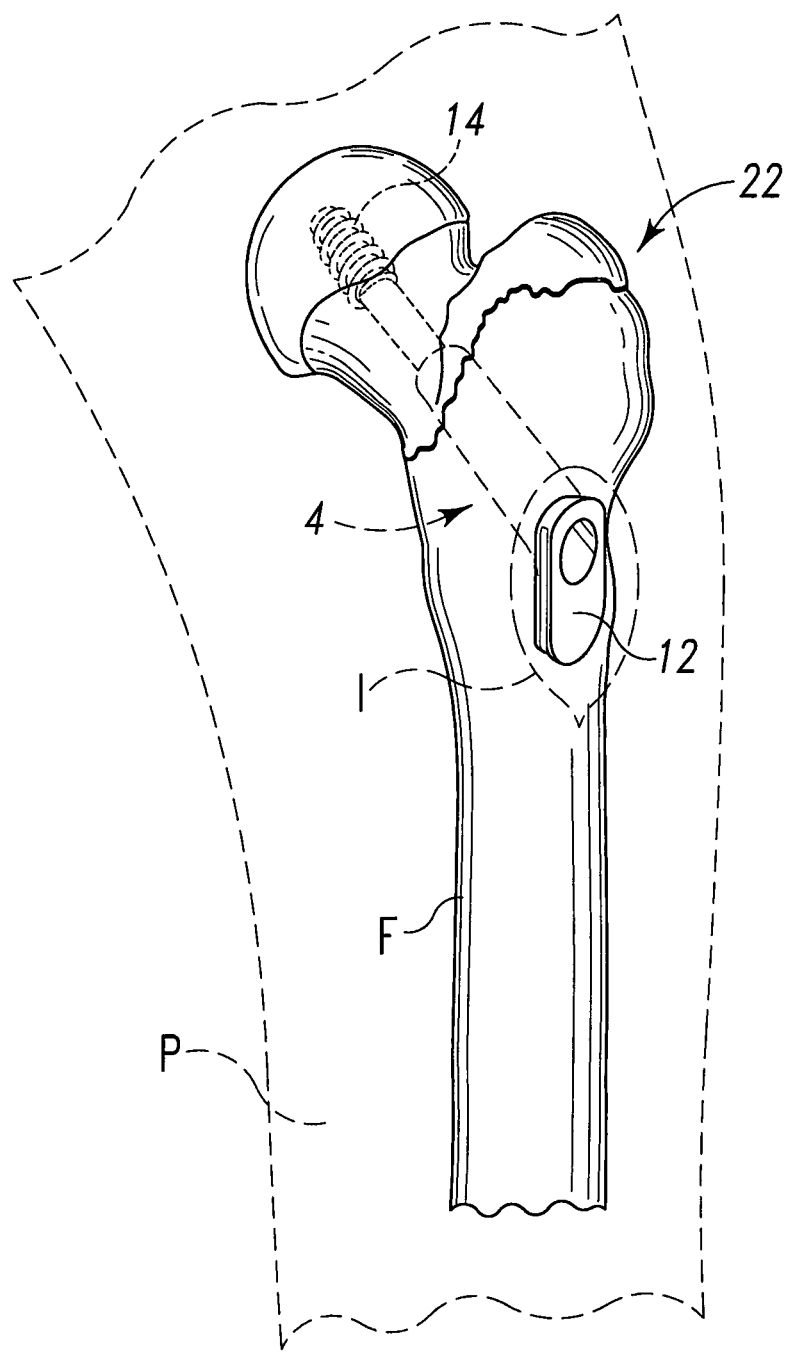
FIG. 4 is a perspective view of the lag screw assembly of FIG. 2A implanted in a femur of a patient according to the present disclosure, with the lag screw assembly being partially visually exposed through an incision in a patient.

At a particular stage during a hip fracture reduction procedure, the lag screw assembly 4 is secured within a femoral head, neck, and shaft of a femur F of a patient P as shown in FIG. 4. The lag screw assembly 4 is partially visually exposed through an incision I in the patient P as shown in FIG. 4. The femur F has a fracture 22 defined therein as shown in FIG. 4.

Figure 36:
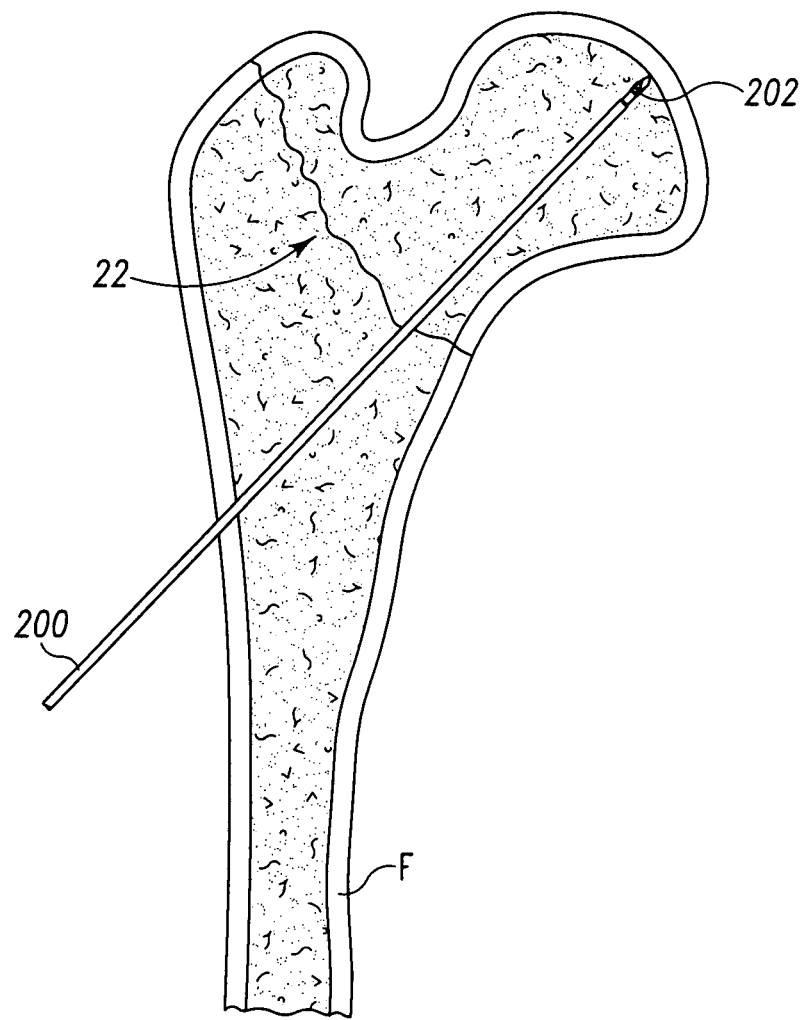
FIG. 36 is a fragmentary side elevational view of the guide wire of FIG. 37 positioned in the femur of FIG. 4, with the femur shown in cross section.

In order to facilitate placement of the lag screw assembly 4 as shown in FIG. 4, a surgeon advances a guide wire 200 into the shaft, neck, and head of the femur F through the incision I to the position shown in FIG. 36. Note the guide wire 200 is advanced until threads 202 of the guide wire 200 are secured to subchondral bone in the center of the head of the femur F in both anterior-posterior and lateral views.

Figure 37:
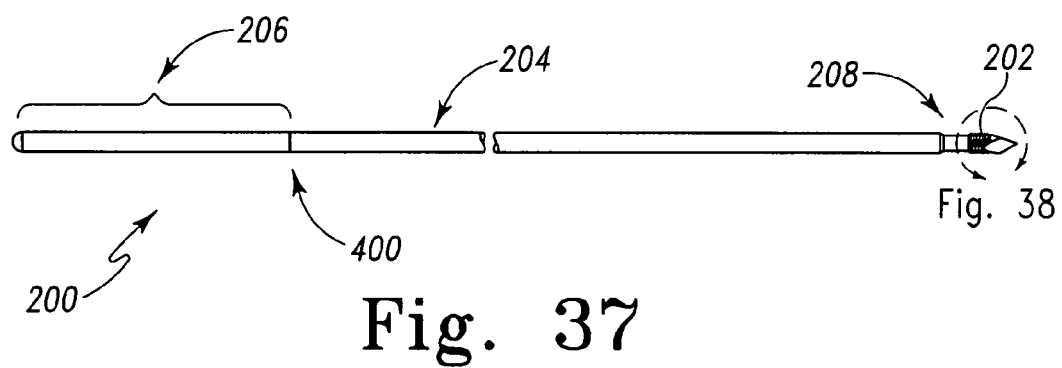
FIG. 37 is a side elevational view of a guide wire which is used to implant the lag screw assembly of FIG. 2A in a minimally invasive manner according to the present disclosure.
Figure 38:
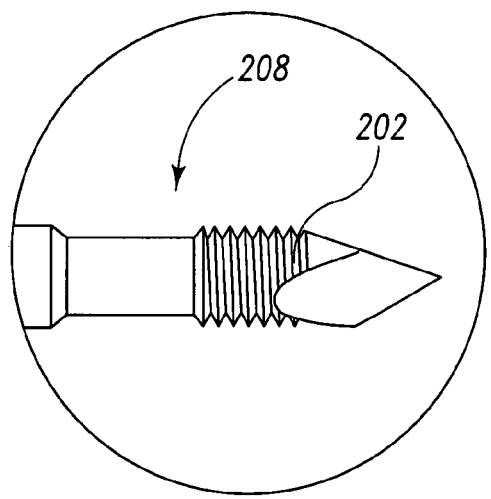
FIG. 38 is an enlarged, side elevational view of the portion of the guide wire of FIG. 37 that is encircled and identified as FIG. 38.

The guide wire 200, which is preferably a 3.2 mm guide wire, is shown in more detail in FIGS. 37-38. The guide wire 200 includes an elongate body 204 having a proximal portion 206 and a distal portion 208. The distal portion 208 includes threads 202 as shown in FIGS. 37-38. The proximal portion 206 is preferably colored black, while the rest of the guide wire 200 is preferably colored metallic gray or silver. The guide wire 200 is preferably made of a radio opaque material such as stainless steel.

Turning now to FIGS. 39-49, there is shown instrumentation that facilitates advancement of the guide wire 200 into the shaft, neck, and head of the femur F through the incision I to the position shown in FIG. 36. In particular, FIGS. 39-43 show a guide component 300 that includes a base 302 and a handle 304. The handle 304 includes a proximal portion 304P and a distal portion 304D. The proximal portion 304P includes a hexagonally-shaped internal surface 312 located within a bore 315 defined the proximal portion 304P (see FIG. 43). The distal portion 304D includes a hexagonally-shaped external surface 314 configured to be received in the bore 315. The external surface 314 is configured complementary to the internal surface 312 so that the external surface 314 mates with the internal surface 316 defined by the bore 315.

The distal portion 304D of the handle 304 is secured to the base 302. The base 302 has a passageway 306 defined therein. The base 302 includes a coupling component 308 located in the passageway 306. The coupling component 308 includes a set of internal threads 310 located in the passageway 306.

Figure 39:
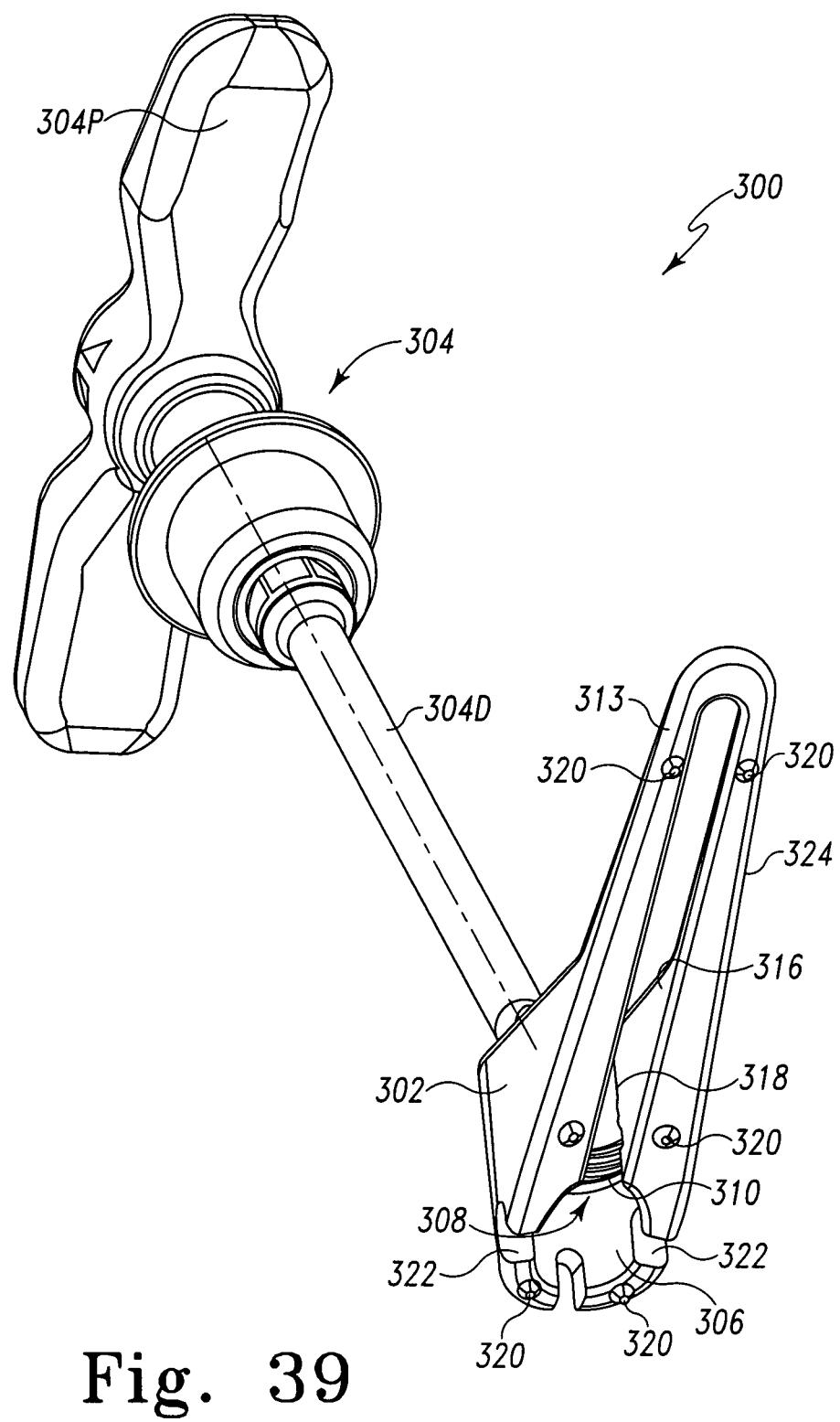
FIG. 39 is a perspective view of a guide component that is used to prepare a fastener cavity in a femur of a patient in a minimally invasive manner according to the present disclosure.
Figure 40:
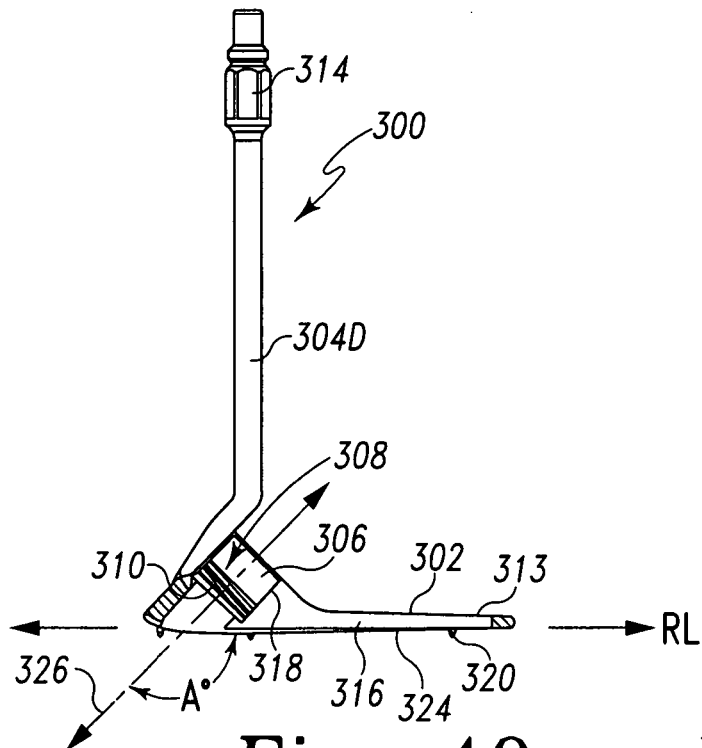
FIG. 40 is a side elevational view of the guide component of FIG. 39, with the proximal portion of its handle shown removed for clarity of viewing.
Figure 42:
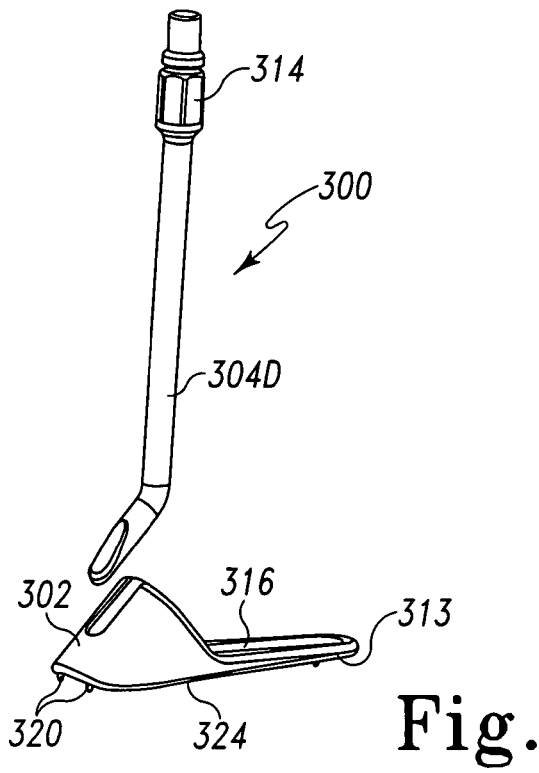
FIG. 42 is an exploded, perspective view of the guide component of FIG. 39, with the proximal portion of its handle shown removed for clarity of viewing.
Figure 43:
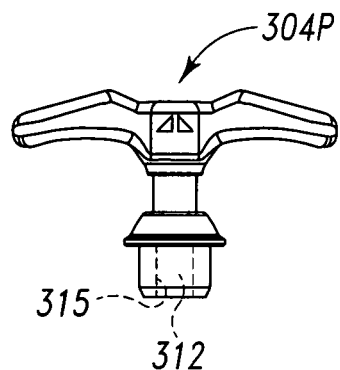
FIG. 43 is a front elevational view of the proximal portion of the handle of the guide component of FIG. 39.

The base 302 includes a finger 313 that has a slot 316 defined therein as shown in FIGS. 39, 40, and 42. The slot 316 extends through the base 302. The slot 316 communicates with the passageway 306. In particular, the slot 316 and the passageway 306 share a common opening 318 through which an object may pass. The existence of the common opening 318 between the passageway 306 and the slot 316 is advantageous when the guide component 300 is being advanced through the incision I (see FIG. 4) over the guide wire 200. Indeed, the common opening 318 allows the guide wire 200 to be initially positioned within the slot 316 during initial advancement of the guide component 300 in relation to the femur F, and then subsequently positioned within the passageway 306 during final positioning of the guide component 300 relative to the femur F. This allows a surgeon to initially manipulate the guide component 300 through the incision I and then subsequently position the guide component appropriately on the femur, in both instances while the guide wire 200 is extending through the base 302.

Figure 41:
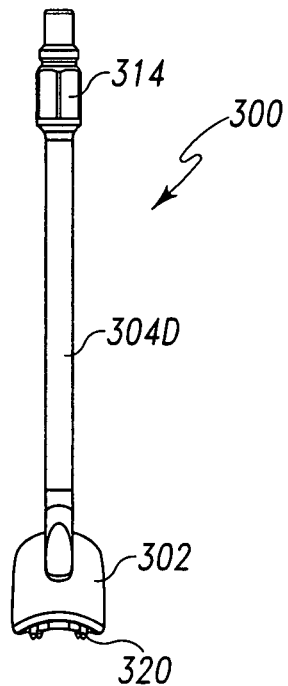
FIG. 41 is a front elevational view of the guide component of FIG. 39, with the proximal portion of its handle shown removed for clarity of viewing.

The base 302 further includes a number of prongs 320 extending distally. The prongs 320 are configured to inhibit relative movement between the guide component 300 and the femur F when the guide component 300 is positioned in contact with the femur F. A plurality of notches 322 are defined in the base 302. Alternatively, the notches 322 may be omitted from the design as shown in FIGS. 40-42.

The base 302 further includes a contact surface 324 that contacts the femur F during use of the guide component 300. The contact surface 324 defines a reference line RL as shown in FIG. 40. The passageway 306 defines a central axis 326 that intersects the reference line RL to define an angle A. The angle A in the embodiment shown in FIG. 40 has a magnitude of 135°.

During the performance of a hip reduction procedure, the surgeon would be provided with a kit (not shown) containing various instrumentation and implants that include a plurality of guide components 300 that are identical to each other except with respect to the magnitudes of their angles A. In particular, each of the guide components 300 supplied in the kit would include a distinct angle A in comparison to each other. For example, the kit may include four guide components 300, the first guide component would be configured with an angle A having a magnitude of 125°, while the second guide component would be configured with an angle A having a magnitude of 130°. And the third guide component would be configured with an angle A having a magnitude of 135°, while the fourth guide component would be configured with an angle A having a magnitude of 140°. The surgeon would measure or otherwise determine the neck angle of the femur F, and then select from the kit the guide component having the angle A that best matches the anteversion angle of the femur.

Turning now to FIGS. 44-46, there is shown a sheath 327 that defines a passageway 328 extending therethrough. The passageway 328 defines a central axis 329. The sheath 328 includes a coupling component 330 that is configured to cooperate with the coupling component 308 of the guide component 300 to couple the sheath 327 to the base 302 of the guide component. In particular, the coupling component 330 includes a set of external threads 332 defined on an outer surface 334 of the sheath 327. The set of external threads 332 of the sheath 327 are configured to meshingly engage the set of internal threads 310 of the base 302 so as to secure the sheath 327 to the guide component 300. When the set of external threads 332 are meshingly engaged with the set of internal threads 310, the passageway 306 of the guide component 300 is aligned with the passageway 328 of the sheath 327. Further, when the set of external threads 332 are meshingly engaged with the set of internal threads 310, the central axis 326 of the passageway 310 is aligned with the central axis 329 of the sheath 327.

Figure 47:
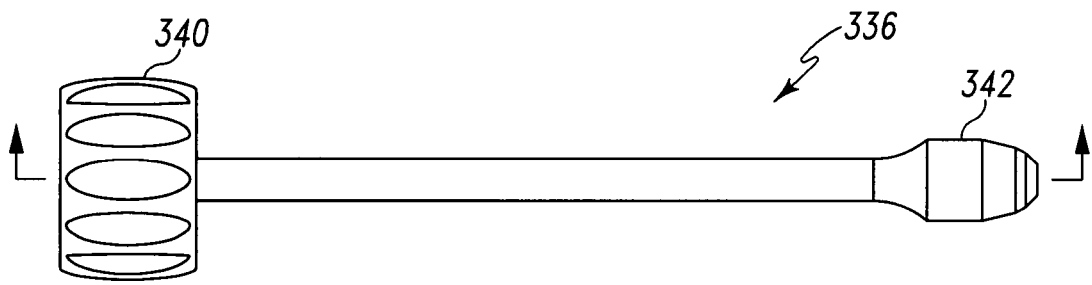
FIG. 47 is a side elevational view of another sheath that is used to place a guide wire in a femur of a patient in a minimally invasive manner according to the present disclosure.
Figure 48:
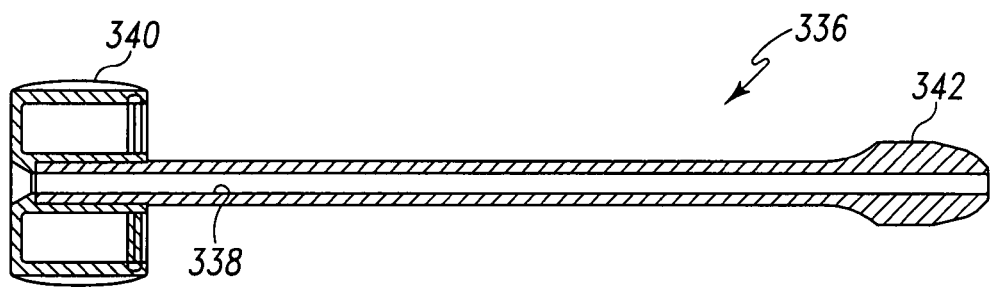
FIG. 48 is a cross sectional view of the sheath of FIG. 47.
Figure 49:
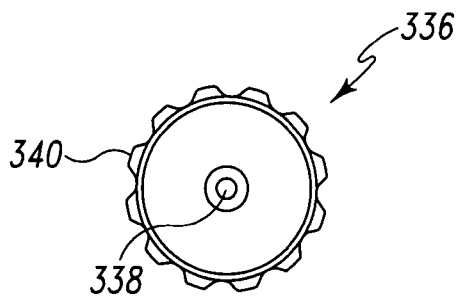
FIG. 49 is an end elevational view of the sheath of FIG. 47.

Referring now to FIGS. 47-49, there is shown another sheath 336 defining a passageway 338 therethrough. The sheath 336 includes a knob 340 located at a proximal portion of the sheath 336, and a bulbous segment 342 located at a distal portion of the sheath 336. The sheath 336 is configured to be positioned in the passageway 328 of the sheath 327. During use of the instrumentation by a surgeon, the guide wire 200 extends through the passageway 338 of the sheath 336, and the sheath 336 is positioned within the passageway 328 of the sheath 327. The bulbous segment 342, as well as the knob 340, facilitates centering of the sheath 336 within the passageway 328 of the sheath 327. The sheath 336 may be provided with one or more additional bulbous segments (not shown) in order to further facilitate centering of the sheath 336 within the passageway 328 of the sheath 327. Such additional bulbous segment(s) may be located at an intermediate portion of the sheath 336 between the knob 340 and the bulbous segment 342.

Turning to FIGS. 50-54, there is shown a stop structure 350 defining a central passage 352. The stop structure 350 includes a gripping portion 353. The stop structure 350 further includes an external surface 354 that defines a number of keyways 356. The keyways 356 include a first keyway group 356A that are aligned in a first row lengthwise of the stop structure 350. The keyways 356 also include a second keyway group 356B that are aligned in a second row lengthwise along the stop structure 350.

Figure 54:
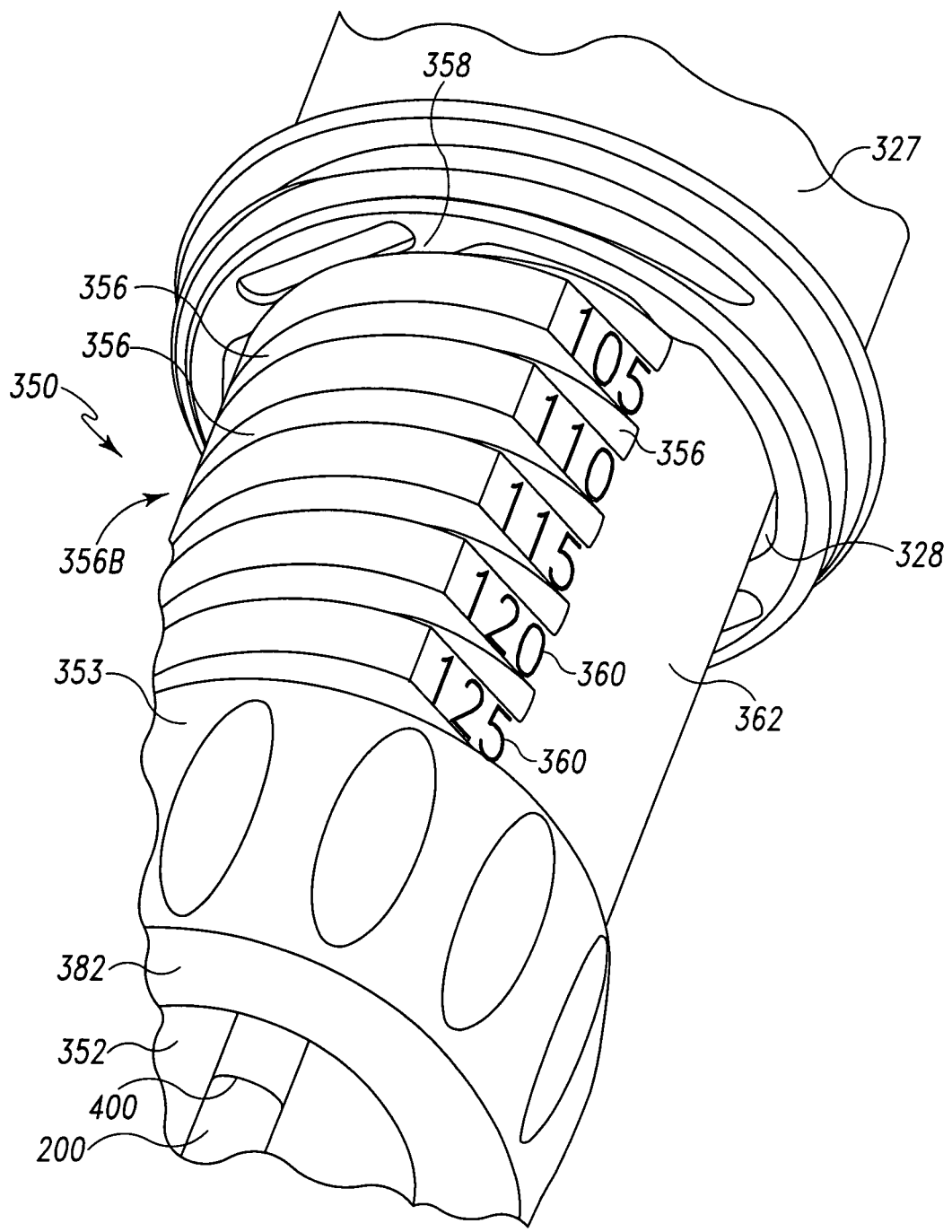
FIG. 54 is a fragmentary, enlarged view of the stop structure of FIG. 50 shown partially positioned within the sheath of FIG. 44.

As shown in FIGS. 45-46, the sheath 327 includes a number of key members 358 positioned on a proximal portion of the sheath. Each key member 358 is configured to be selectively received in any one of the keyways 356. For example, as shown in FIG. 54, the key member 358 is shown received in the keyway 356 associated with an indicia marking "105". When a key member 358 is received in a keyway 356 (or when both key members 358 are received within respective keyways 356), the stop structure 350 is fixed in relation to the sheath 327.

Figure 50:
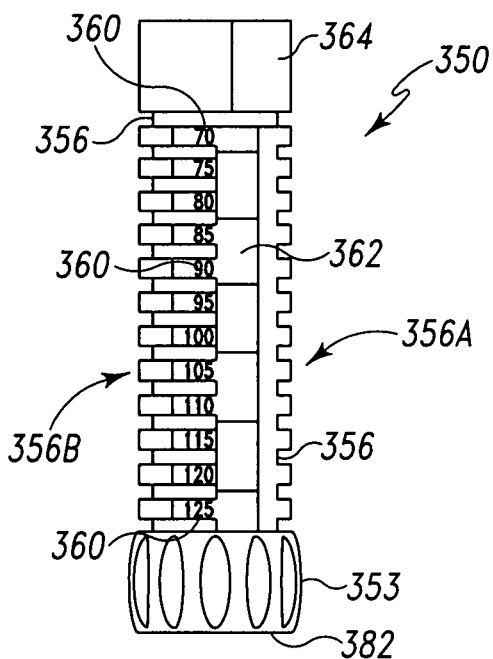
FIG. 50 is a side elevational view of a stop structure that is used to prepare a fastener cavity in a femur of a patient in a minimally invasive manner according to the present disclosure.

The stop member 350 further includes a plurality of indicia markings 360 respectively associated the plurality of keyways 356. In particular, as shown in FIG. 50, the indicia markings "70", "75", "80", "85", "90", "95", "100", "105", "110", "115", "120", and "125" are respectively located adjacent the second keyway group 356B. Similarly, the indicia markings "70", "75", "80", "85", "90", "95", "100", "105", "110,", "115", "120", and "125" (not shown) are respectively located adjacent the first keyway group 356A in the same manner the indicia markings are positioned adjacent to the second keyway group 356B. By positioning the indicia markings 360 respectively adjacent to the plurality of keyways 356, the indicia markings are respectively positioned in association with the keyways 356 so that a user of the stop structure 350 is informed that the respective indicia marking 360 represents a value associated with the respective keyway 356. As will be discussed in more detail below, the values represented by indicia markings 360 relate to possible lengths of a lag screw assembly (e.g. lag screw assembly 4) in millimeters.

Figure 51:
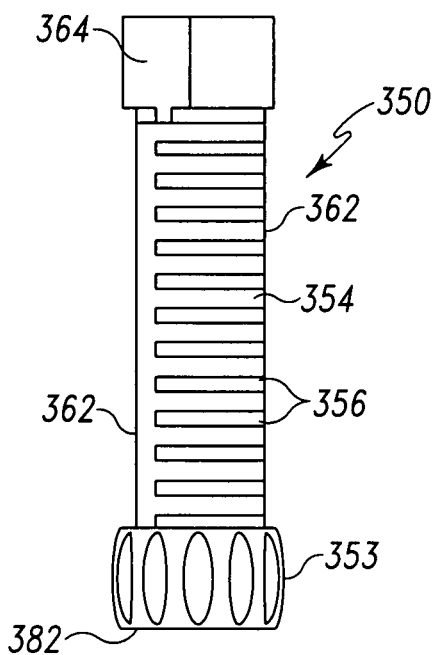
FIG. 51 is another side elevational view of the stop structure of FIG. 50.
Figure 52:
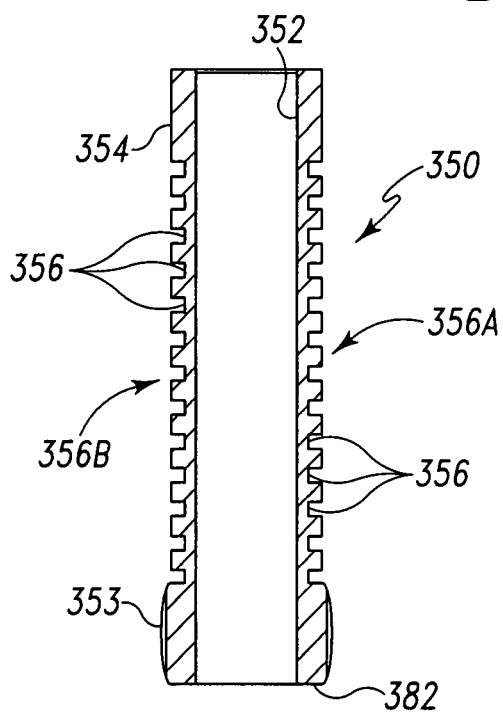
FIG. 52 is a cross sectional view of the stop structure of FIG. 50.
Figure 53:
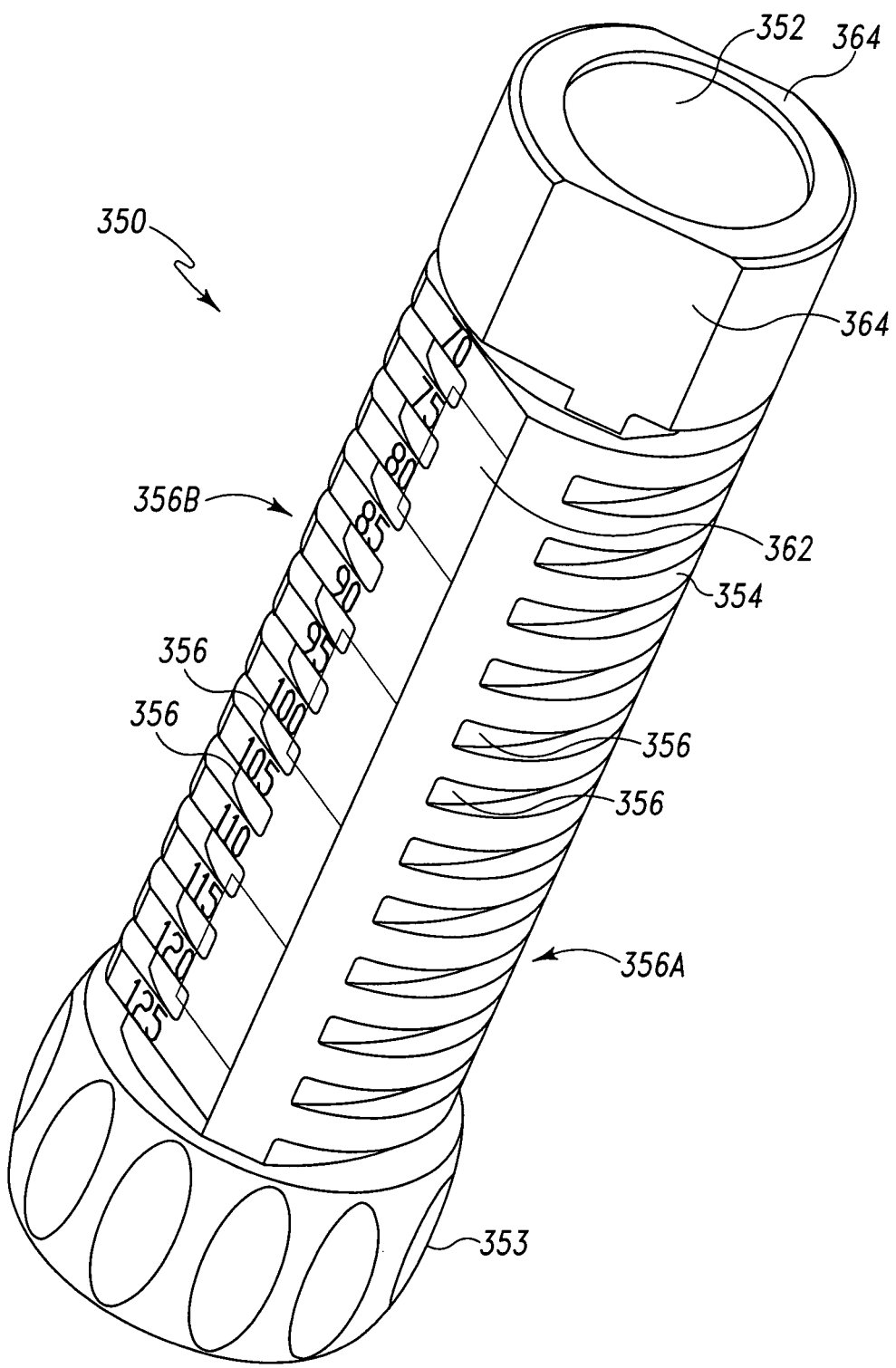
FIG. 53 is a perspective view of the stop structure of FIG. 50.

The stop structure 350 further includes a pair of flat exterior surface portions 362 that extends lengthwise of the stop structure as shown in FIGS. 50, 51, 53, and 54. The flat exterior surface portions 362 are circumferentially offset from each other by 180°. The stop structure 350 also includes another pair of flat exterior surface portions 364 that is located on a distal portion of the stop structure as shown in FIGS. 50, 51, and 53. The flat exterior surface portions 364 are circumferentially offset from each other by 180°. The pair of flat exterior surface portions 362 is circumferentially offset from the pair of flat exterior surface portions 364 as shown in FIGS. 50, 51, and 53.

It should be appreciated that the stop structure 350 is axially movable in relation to the sheath 327 when both (i) the stop structure 350 is at least partially received within the passageway 328 of the sheath, and (ii) the key members 358 of the sheath 327 are respectively aligned with the pair of flat exterior surface portions 362 of the stop structure 350. Similarly, the stop structure 350 is axially movable in relation to the sheath 327 when both (i) the stop structure 350 is at least partially received within the passageway 328 of the sheath, and (ii) the key members 358 of the sheath 327 are respectively aligned with the pair of flat exterior surface portions 364 of the stop structure 350.

Figure 55:
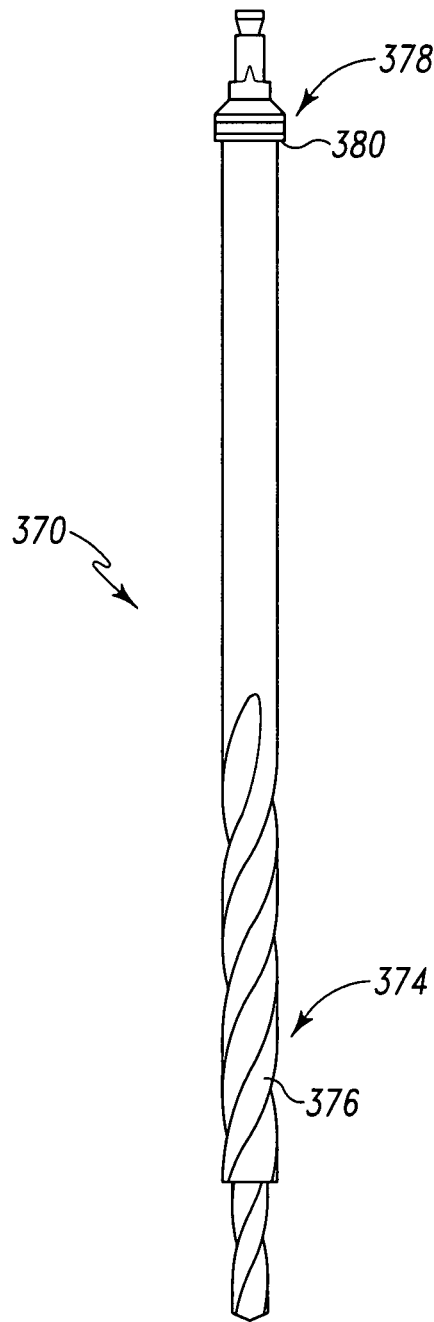
FIG. 55 is a side elevational view of a drill (with its handle removed) that is used to prepare a fastener cavity in a femur of a patient in a minimally invasive manner according to the present disclosure.
Figure 56:
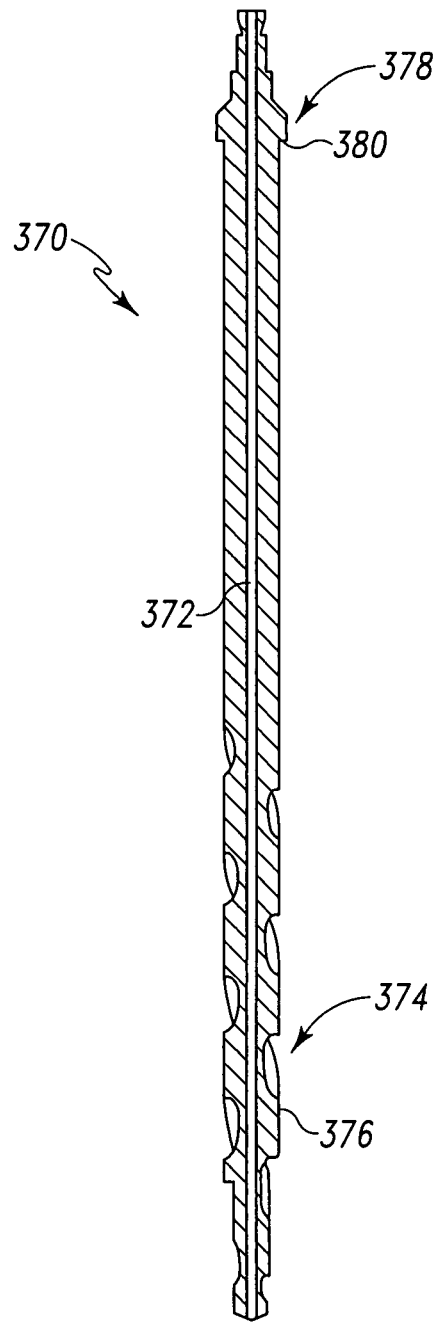
FIG. 56 is a cross sectional view of the drill of FIG. 55.

Referring now to FIGS. 55-56, there is shown a drill 370 defining a passageway 372 therethough. The drill 370 includes a distal portion 374 defining a cutting surface 376. The drill 370 further includes a proximal portion 378 having a shoulder 380. During use, the drill 370 is advanced over the guide wire 200 so that the guide wire is positioned in the passageway 372. The drill 370 is further advanced over the guide wire 200 so as to position the drill 370 in the central passage 352 of the stop structure 350 while the stop structure is axially fixed in relation to the sheath 327. During advancement of the drill 370 through the central passage 352, the shoulder 380 of the drill 370 comes into contact with a proximal surface 382 of the stop structure 350. Contact between the shoulder 380 of the drill and the proximal surface 382 of the stop structure prevents further advancement of the drill within the central passage 352 of the stop structure, thereby limiting further penetration of the drill 370 into the femur F.

Referring now to FIGS. 57-59, there is shown a tap 386 defining a passageway 388 therethough. The tap 386 includes a distal portion 390 defining a cutting surface 392. The tap 386 further includes a proximal portion 394 having a shoulder 396. During use, the tap 386 is advanced over the guide wire 200 so that the guide wire is positioned in the passageway 388. The tap 386 is further advanced over the guide wire 200 so as to position the tap 386 in the central passage 352 of the stop structure 350 while the stop structure is axially fixed in relation to the sheath 327. During advancement of the tap 386 through the central passage 352, the shoulder 396 of the tap 386 comes into contact with a proximal surface 382 of the stop structure 350. Contact between the shoulder 396 of the tap and the proximal surface 382 of the stop structure prevents further advancement of the tap within the central passage 352 of the stop structure, thereby limiting further penetration of the tap 386 into the femur F.

Figure 5:
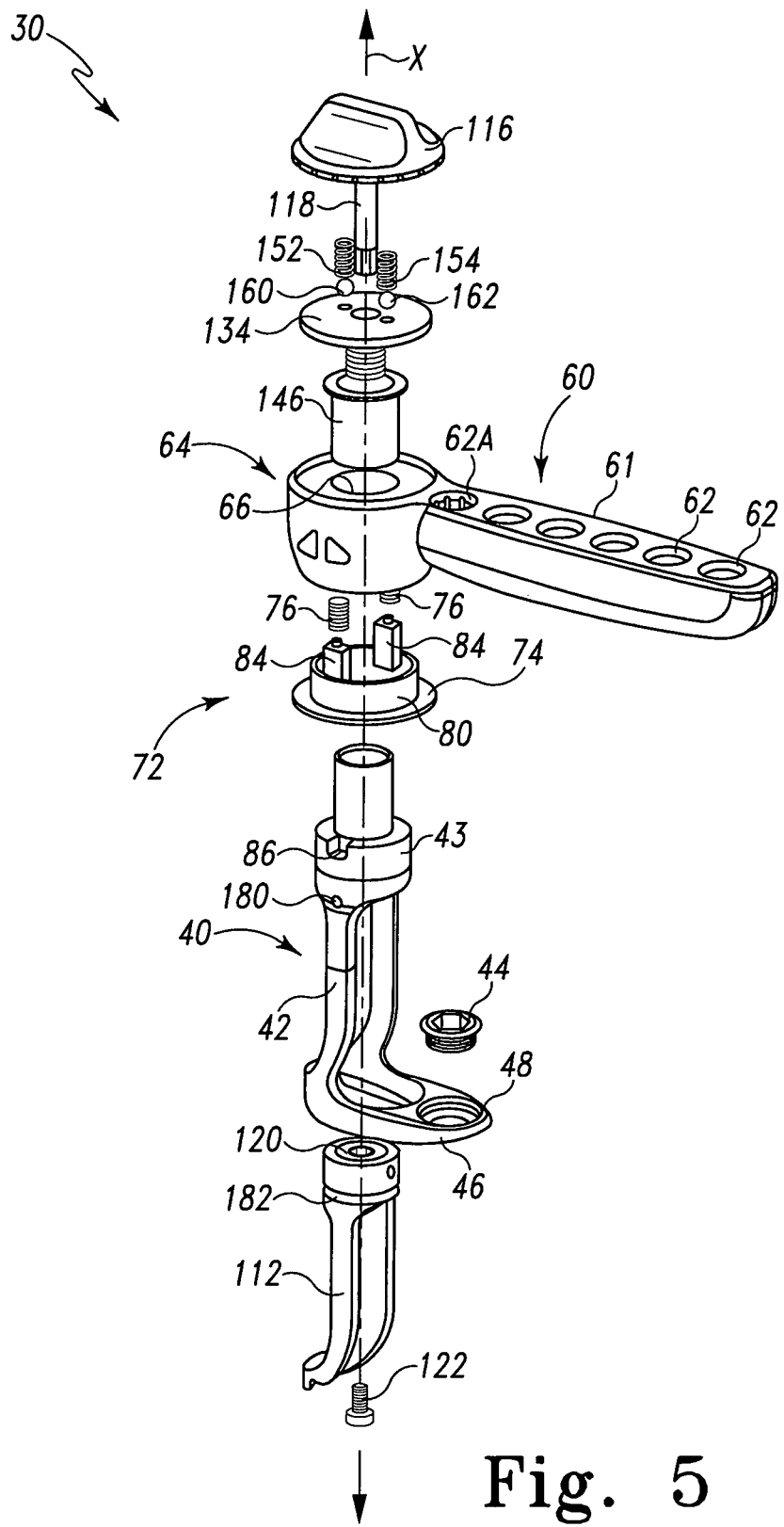
FIG. 5 is an exploded, perspective view of an instrument assembly (with the implant assembly not shown) that is used to implant the implant assembly of FIG. 1 in the patient in a minimally invasive manner according to the present disclosure.
Figure 6:
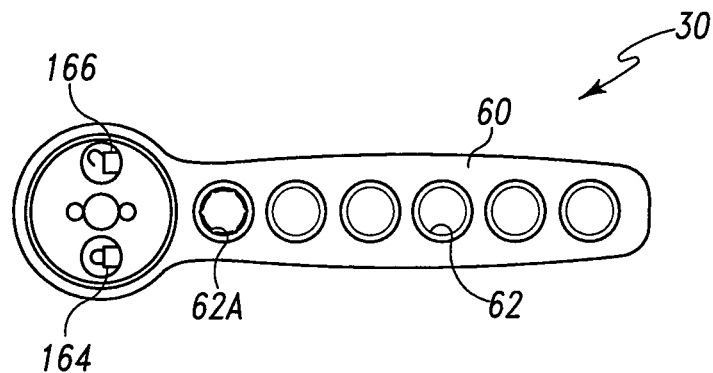
FIG. 6 is a top elevational view of the instrument assembly of FIG. 5, with the knob of the instrument assembly removed for clarity of viewing.
Figure 7:
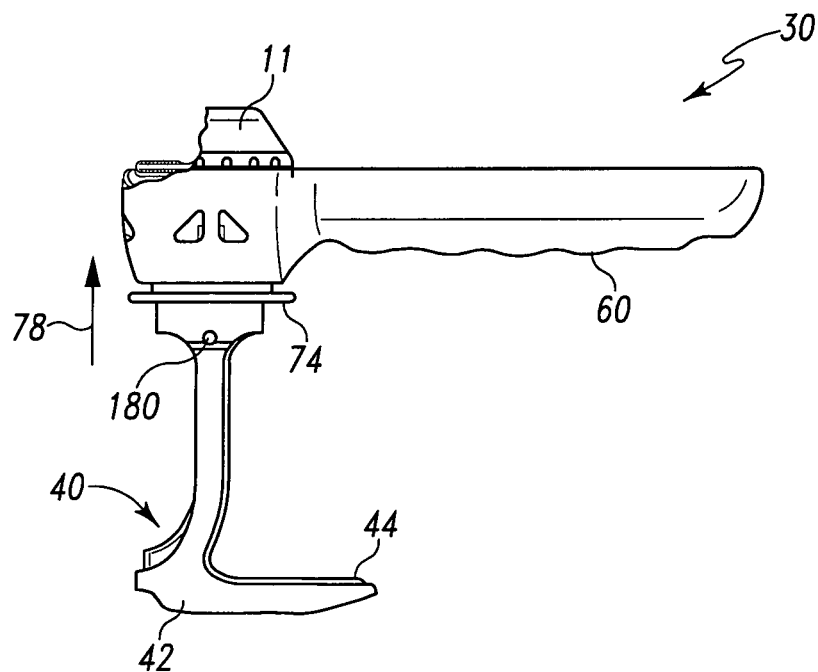
FIG. 7 is a side elevational view of the instrument assembly of FIG. 5, with the implant assembly not shown.
Figure 8:
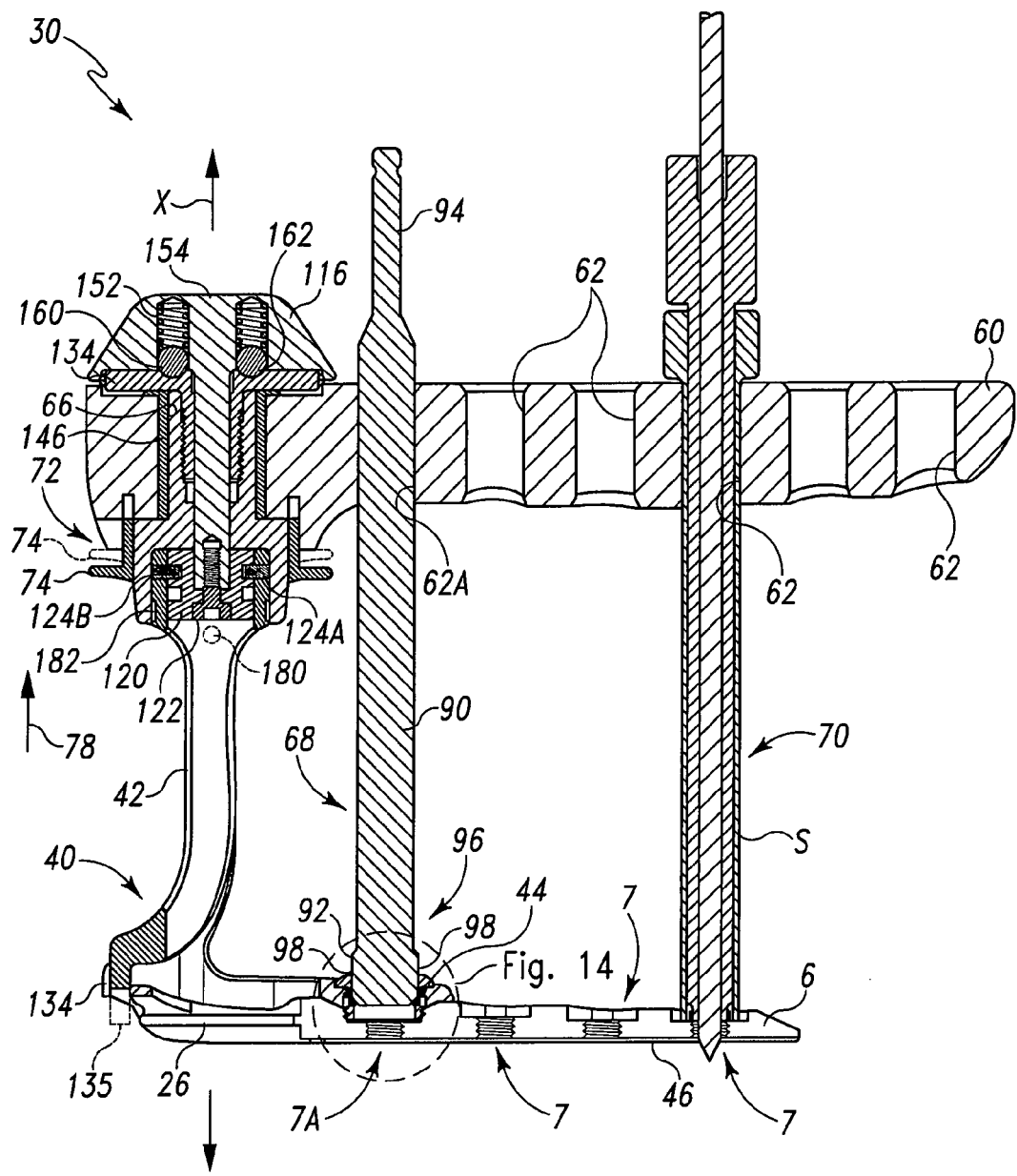
FIG. 8 is a cross sectional view of the instrument assembly of FIG. 5, with the implant assembly shown.

Turning now to FIGS. 5-7, there is shown an instrument assembly 30 that is used to facilitate implantation of the bone plate 6 and the bone screws 8A, 8B of the implant assembly 2 into the patient P. FIG. 8 also shows the instrument assembly 30, and a couple of other devices supported thereby.

Figure 14:
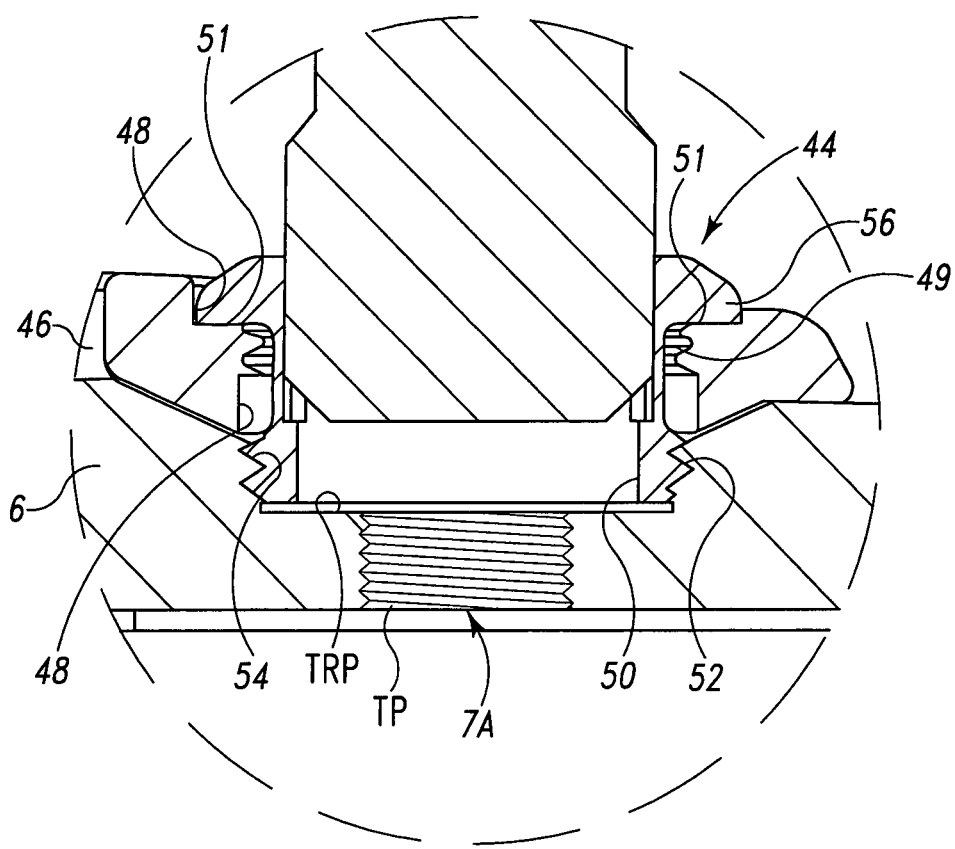
FIG. 14 is an enlarged, fragmentary, cross sectional view of the instrument assembly showing the portion of FIG. 8 that is encircled and identified as FIG. 14.

The instrument assembly 30 includes a plate holder 40 having a body 42 and a coupling component 44 rotatably supported by the body 42. The body 42 is also shown in FIGS. 9-10, while the coupling component 44 is also shown in FIGS. 11-13. The body 42 includes a foot portion 46 that defines a passage 48. The body 42 further includes a neck 43. The foot portion 46 includes a set of internal threads 49 located within the passage 48 as shown in FIG. 14. The coupling component 44 has defined therein a passage 50 extending therethrough. The coupling component 44 includes a flange 45 and a set of external threads 52 that is configured to meshingly engage with the set of internal threads 49 of the foot portion 46. The set of external threads 52 of the coupling component 44 is also configured to meshingly engage with a set of internal threads 54 defined in the bone plate 6 as shown in FIG. 14.

In order to assemble the coupling component 44 to the foot portion 46, the coupling component 44 is advanced into the passage 48 of the foot portion until the set of external threads 52 of the coupling component 44 contact the set of internal threads 49 of the foot portion 46. Thereafter, the coupling component 44 is rotated so that the set of external threads 52 meshing engagement with the set of internal threads 49 of the foot portion 46. Continued rotation of the coupling component 44 in relation to the foot portion 46 results in advancement of the set of external threads 52 through the set of internal threads 49. After the set of external threads 52 are advanced through the set of internal threads 49, the coupling component 44 is rotatably attached to the foot portion 46. In this assembled state, the coupling component 44 is able to rotate freely in relation to the foot portion 46. Further, the coupling 44 is able to move a distance axially within the passage 48, but is prevented from becoming detached from the foot portion 46. Indeed, upward movement of the coupling component 44 in relation to the foot portion 46 is limited by interaction of the set of external threads 52 of the coupling component and the set of internal threads 49 of the foot portion. Also, downward movement of the coupling component 44 in relation to the foot portion 46 is limited by interaction of the flange 56 of the coupling component and a shoulder 51 of the foot portion which is located in the passage 48.

Note that when the set of external threads 52 of the coupling component 44 are mated with the set of internal threads 54 of the bone plate 6, the bone plate 6 is secured to the foot portion 44 of the plate holder 40. Also note that when the set of external threads 52 of the coupling component 44 are mated with the set of internal threads 54 of the bone plate 6, the passageway 50 of the coupling component 44 is aligned with the fastener opening 7A of the bone plate 6.

Figure 15:
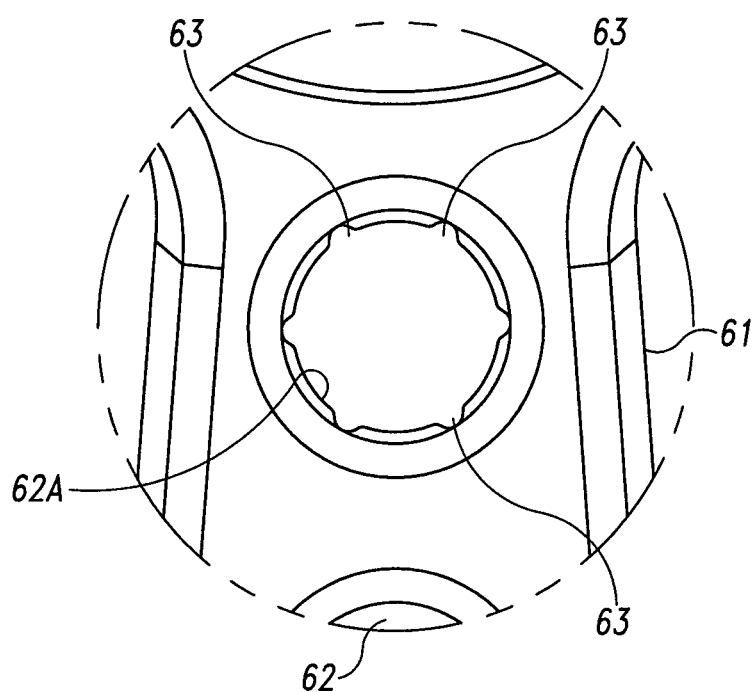
FIG. 15 is an enlarged, fragmentary, top elevational view of the guide component of the instrument assembly of FIG. 5.
Figures 23, 24:
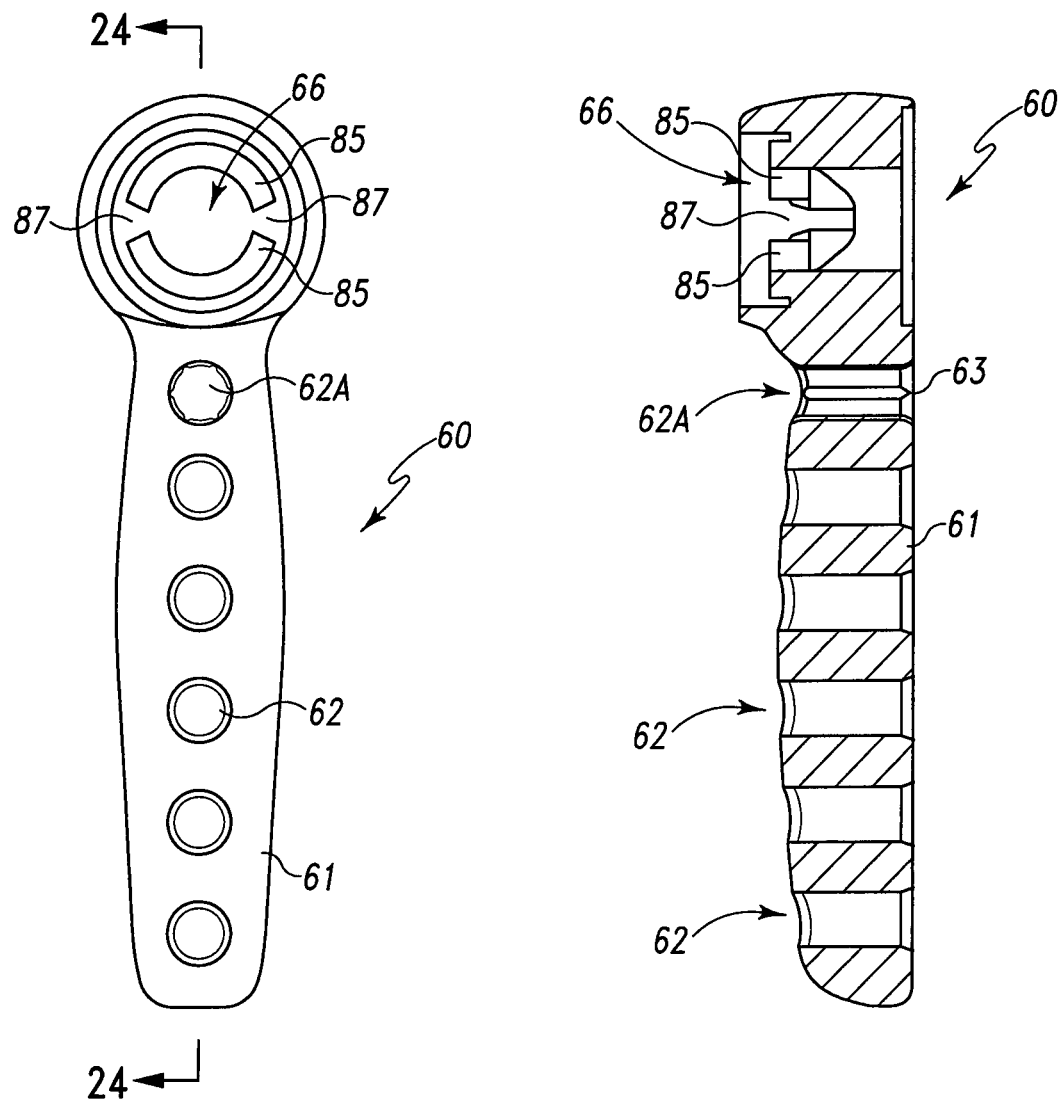
FIG. 23 is a bottom elevational view of a guide component of the instrument assembly of FIG. 5.
FIG. 24 is a cross sectional view of the guide component taken along the line 24-24 of FIG. 23.

As shown in FIGS. 5-8, the instrument assembly 30 further includes a guide component 60 that is pivotably secured to the body 42 of the plate holder 40. The guide component 60 includes a handle portion 61 having defined therein a plurality of guide holes 62, 62A. The handle portion further defines a plurality of peripheral slots 63 that are located in the guide hole 62A as shown in FIGS. 5 and 15. The guide component 60 further includes an end portion 64 that includes a cavity 66 defined therein as shown in FIGS. 23-24.

Figure 16:
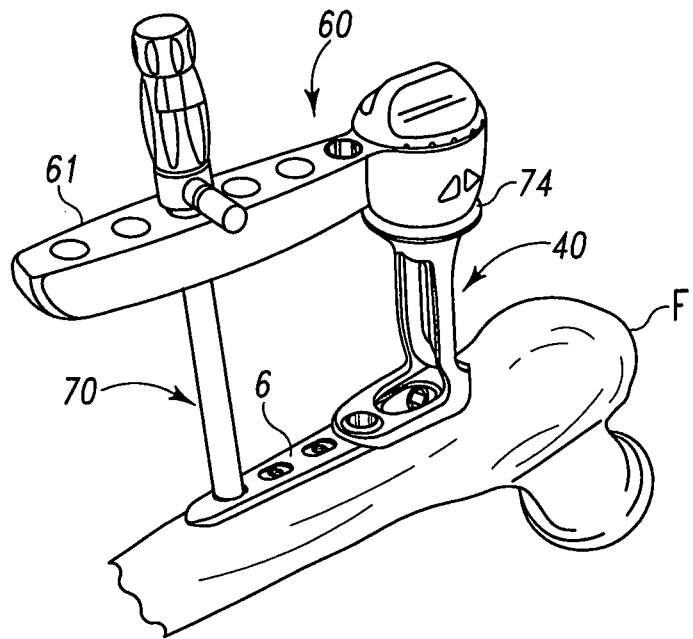
FIG. 16 is a perspective view of the instrument assembly of FIG. 5 (with the implant assembly attached thereto) and being used to implant the implant assembly in a femur according to the present disclosure, with the femur and the implant assembly being shown removed from the body of a patient P for clarity of viewing.
Figure 17:
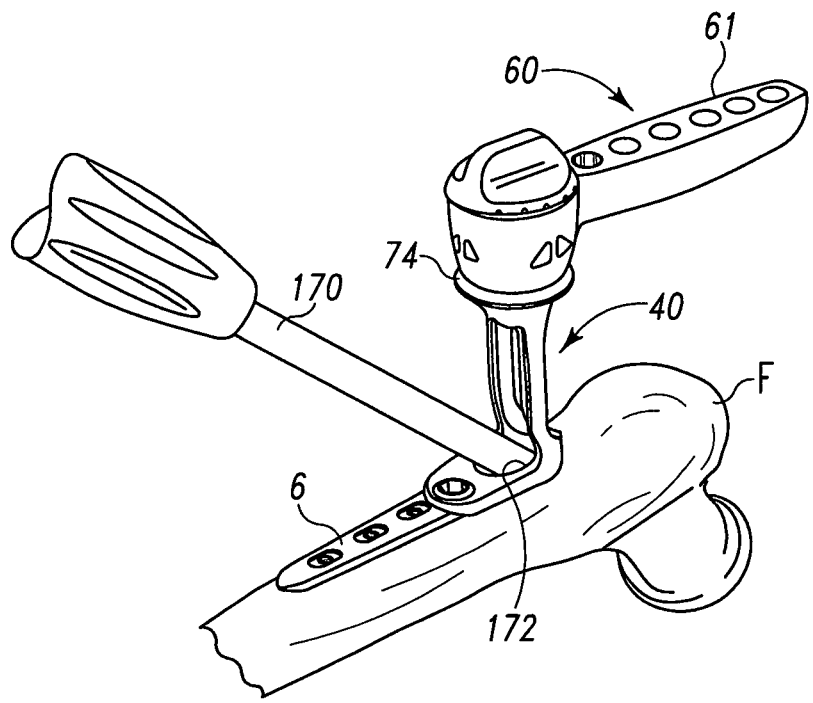
FIG. 17 is another perspective view of the instrument assembly of FIG. 5 (with the implant assembly attached thereto) and being used to implant the implant assembly in a femur according to the present disclosure, with the femur and the implant assembly being shown removed from the body of a patient P for clarity of viewing.
Figures 18, 19:
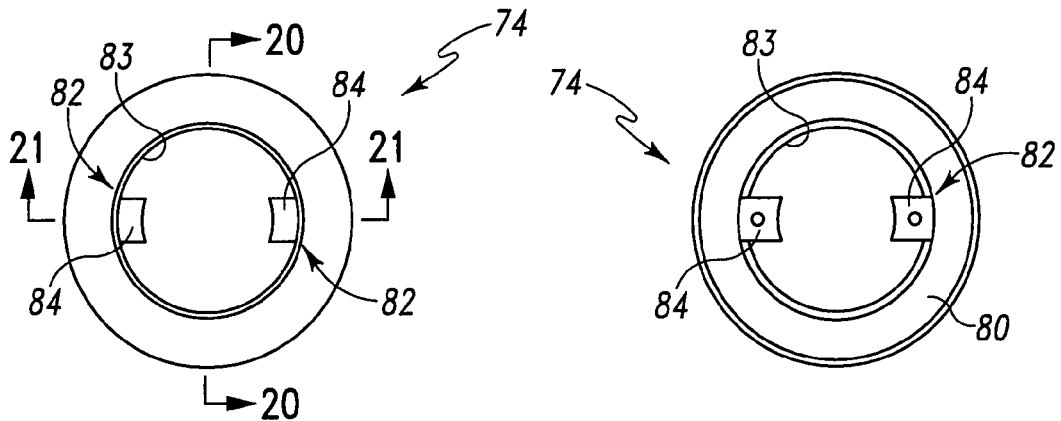
FIG. 18 is a bottom elevational view of an actuator of the instrument assembly of FIG. 5.
FIG. 19 is a top elevational view of the actuator of FIG. 18.
Figures 20, 21:
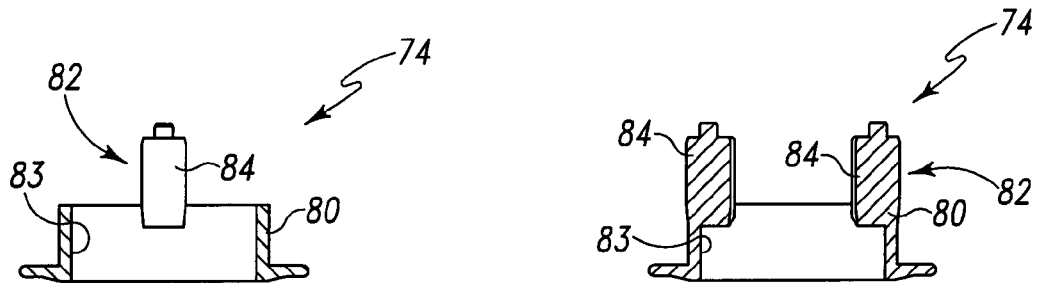
FIG. 20 is a cross sectional view of the actuator taken along the line 20-20 of FIG. 18.
FIG. 21 is a cross sectional view of the actuator taken along the line 21-21 of FIG. 18.

Since the guide component 60 is pivotably connected to the plate holder 40, the guide component 60 is movable in relation to the body 42 of the plate holder 40 between a first position shown in FIG. 16 (see also FIGS. 7-8) and a second position shown in FIG. 17. The guide component 60 pivots about an axis X. (See FIGS. 5 and 8.) Pivoting the guide component 60 180° about the axis X causes the guide component 60 to move from its first position (see FIG. 16) to its second position (see FIG. 17).

When the guide component 60 is located at its first position in relation to the plate holder 40 (see FIG. 16), the plurality of guide holes 62, 62A are respectively aligned with the plurality of fastener openings 7, 7A. For example, as shown in FIG. 8, the left most guide hole 62A is aligned with the left most fastener opening 7A so that an elongate instrument (e.g. a driver 68) may be advanced through the guide hole 62A and present its working end at the fastener opening 7A. Further, for example, as shown in FIG. 8, the fourth guide hole 62 (from the left) is aligned with the fourth fastener opening 7 (from the left) so that an elongate instrument (e.g. a drill assembly 70) may be advanced through the guide hole 62 and present its working end at the fastener opening 7. When the guide component 60 is located at its second position in relation to the plate holder 40 (see FIG. 17), the plurality of guide holes 62, 62A are respectively misaligned with the plurality of fastener openings 7, 7A. Indeed, advancing elongate instruments 68, 70 respectively through the guide holes 62, 62A would not result in the working ends of the elongate instruments being respectively presented at the fastener openings 7, 7A.

Moreover, as can be seen from FIGS. 16 and 17, when the guide component 60 is positioned at its first position in relation to the plate holder 40 (see FIG. 16), the handle portion 61 is positioned over the bone plate 6. On the other hand, when the guide component 60 is positioned at its second position in relation to the plate holder 40 (see FIG. 17), the handle portion 61 is not positioned over the bone plate 6. Positioning of the guide component 60 at its second position (see FIG. 17) facilitates visibility of the bone plate 6 and surrounding area. Moreover, positioning of the guide component 60 at its second position (see FIG. 17) facilitates access of instruments and other devices to the bone plate 6 and surrounding area.

Figure 22:
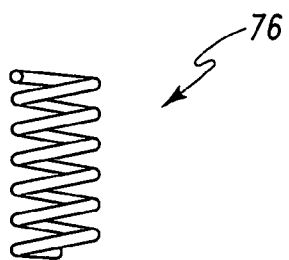
FIG. 22 is a side elevational view of a spring 76 of the instrument assembly of FIG. 5.

The instrument assembly 30 further includes a locking mechanism 72 that is configured to lock the guide component 60 in relation to the body 42 of the plate holder 40 at its first position as shown in FIG. 16, and at its second position as shown in FIG. 17. The locking mechanism 72 includes an actuator 74 that is partially located in the cavity 66 of the guide component 60. The actuator 74 is movable between a lower position (shown in solid in FIG. 8), and an upper position (shown in phantom in FIG. 8). The locking mechanism 72 includes a plurality of springs 76 configured to bias the actuator 74 toward its lower position. (See FIG. 8.) The springs 76 have an identical configuration with respect to each other, and one spring 76 is shown in FIG. 22. The springs 76 are located in the cavity 66 of the guide component 60. Within the cavity 66, the springs 76 are interposed between the actuator 74 and the guide component 60. In order to move the actuator 74 from its lower position to its upper position against the spring bias of the springs 76, force is applied to the actuator in the direction of arrow 78 thereby urging the actuator upwardly until the actuator 74 contacts a lower surface of the guide component 60. Thereafter, in order to move the actuator 74 from its upper position to its lower position, the upwardly applied force is removed thereby allowing the springs 76 to urge the actuator 74 downwardly to its lower position.

When the actuator 74 is positioned in its lower position, the guide component 60 is locked in relation to the body 42 of the plate holder 40 at its first position (shown in FIG. 16). Thereafter, an upward force is applied to the actuator 74 in the direction of arrow 78 thereby moving the actuator from its lower position (shown in solid in FIG. 8) to its upper position (shown in phantom in FIG. 8). When the actuator 74 is positioned in its upper position, the guide component 60 is free to rotate in relation to the body 42 of the plate holder. Force is then applied to the guide component 60 so that the guide component 60 pivots 180° about the axis X causing the guide component 60 to move from its first position (shown in FIG. 16) to its second position (shown in FIG. 17). Thereafter, the upward force is removed from the actuator 74 thereby allowing the springs 76 to urge the actuator 74 downwardly to its lower position. When the actuator 74 is positioned in its lower position, the guide component 60 is locked in relation to the body 42 of the plate holder 40 at its second position (shown in FIG. 17).

As shown in FIGS. 18-21, the actuator 74 includes a body 80 and a blocking structure 82 supported by the body 80. The body 80 defines a passage 83 therethrough. The blocking structure 82 includes a number of detents 84 attached to the body 80. The body 42 of the plate holder 40 has defined therein a number of detent recesses 86. (See FIGS. 5 and 9.) As shown in FIGS. 23-24, the guide component 60 includes a number of internal walls 85 that are positioned within the passage 66. The internal walls 85 define a number of slots 87.

When the instrument assembly 30 is in an assembled state, the body 80 of the actuator 74 is positioned around the neck 43 of the plate holder 40 so that the neck 43 extends through the passage 83 of the body 80 of the actuator 74 as shown in FIG. 8. The detents 84 are located within the slots 87 of the guide component 60. Thus, the actuator 74 is able to move in the direction of axis X since the detents 84 are able to slide axially within the slots 87, however, the internal walls 85 of the guide component 60 prevent rotation of the actuator 74 in relation to the guide component 60. Thus, the actuator 74 is rotationally fixed in relation to the guide component 60.

When the actuator 74 is positioned at its lower position (shown in solid in FIG. 8), the blocking structure 82 is located in the number of detent recesses 86. In particular, one detent 84 is positioned in one detent recess 86, while another detent 84 is positioned in another detent recess 86. As a result, rotation of the actuator 74 in relation to the body 42 of the plate holder 40 is prevented when the actuator 74 is positioned at its lower position. And since the actuator 74 is rotationally fixed in relation to the guide component 60, the guide component 60 is prevented from rotating in relation to the body 42 of the plate holder 40 when the actuator 74 is positioned at its lower position.

In contrast, when the actuator 74 is positioned at its upper position (shown in phantom in FIG. 8), the blocking structure 82 is spaced apart from the number of detent recesses 86. In particular, both detents 84 are spaced apart from both detent recesses 86. Therefore, rotation of the actuator 74 in relation to the body 42 of the plate holder 40 is allowed when the actuator 74 is positioned at its upper position. Thus, the guide component 60 is allowed to be rotated in relation to the body 42 of the plate holder 40 when the actuator 74 is positioned at its upper position. Accordingly, when the actuator 74 is positioned at its upper position, the guide component 60 may be rotated from its position shown in FIG. 16 to its position shown in FIG. 17. Furthermore, when the actuator 74 is positioned at its upper position, the guide component 60 may be rotated from its position shown in FIG. 17 to its position shown in FIG. 16.

Turning again to FIG. 8, the instrument assembly 30 further includes the driver 68. The driver 68 includes a shaft 90. The driver 68 further includes a tip portion 92 attached to the shaft 90 at one end, and a drive portion 94 attached to the shaft 90 at the other end. The drive portion 94 includes a flat drive surface (not shown). The drive portion 94 is configured to be coupled to a chuck of a manual or power drill (not shown). The tip portion 92 includes a drive structure 96. The drive structure 96 includes a plurality of spaced apart linearly extending ribs 98 (see FIG. 8). Note that the coupling component 44 includes a drive structure 100 (see FIGS. 12-13) that is configured to mate with the drive structure 96 of the tip portion 92 when the tip portion 92 is positioned within the passageway 50 of the coupling component 44 as shown in FIG. 8. The drive structure 100 defines a plurality of spaced apart linearly extending slots 102 that is configured to receive respectively the plurality of spaced apart linearly extending ribs 98. It should be appreciated that the slots 102 extend from a proximal end of the coupling component 44 towards the distal end of the coupling component, and terminates prior to arriving at the distal end of the coupling component 44 as shown in FIG. 13. Further, the tip portion 92 of the driver 68 is configured to interact with the structure of the coupling component 44 that defines the slots 102 so that the tip portion 92 of the driver 68 is prevented from being advanced entirely through the passageway 50 of the coupling component 44.

In order to utilize the driver 68 to attach the bone plate 6 to the plate holder 40, the tip portion 92 of the driver needs to be mated with the drive structure 100 of the coupling component 44. To this end, the tip portion 92 is advanced through the guide hole 62A of the guide component 60. As stated above, the handle portion 61 defines a plurality of peripheral slots 63 that are located in the guide hole 62A as shown in FIGS. 5 and 15. In order to advance the tip portion 92 through the guide hole 62A, the plurality of spaced apart ribs 98 of the tip portion are aligned with the plurality of peripheral slots of the handle portion 61. Thereafter, the tip portion 92 is advanced through the guide hole 62A so that the drive structure 96 passes through the peripheral slots 63. Note that the other guide holes 62 of the guide component 60 are not similarly slotted, and are configured to prevent advancement of the tip portion 92 through the guide holes 62. Continued advancement of the tip portion 92 toward the bone plate 6 results in the tip portion 92 being received within the passage 50 of the coupling component 44. When the tip portion 92 is received within the passage 50, the drive structure 96 of the driver 68 is mated with the drive structure 100 of the coupling component 44. When the drive structure 96 of the driver 68 is mated with the drive structure 100 of the coupling component 44, the shaft 90 of the driver 68 extends through the guide hole 62A of the guide component 60.

In order to secure the bone plate 6 to the plate holder 40, the set of external threads 52 of the coupling component 44 of the plate holder 40 are meshingly engaged with the set of internal threads 54 of the bone plate 6. This is accomplished by placing the driver 68 through the guide hole 62A of the guide component 60 and advancing the tip portion 92 of the driver 68 toward the coupling component 44 until the drive structure 96 of the tip portion 92 mates with drive structure 100 of the coupling component 44. Thereafter, the driver 68 is rotated thereby causing the coupling component 44 to be rotated in relation to the bone plate 6. Rotation of the coupling component 44 in relation to the bone plate 6 causes the set of external threads 52 of the coupling component 44 to be meshingly engaged with the set of internal threads 54 of the bone plate 6 thereby securing the bone plate 6 to the plate holder 40.

Figure 25:
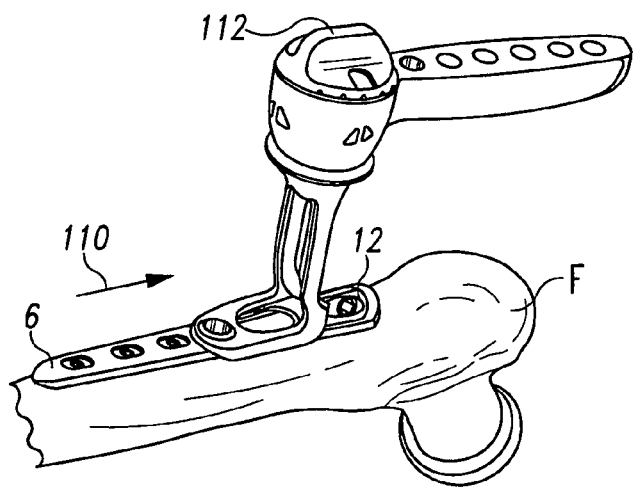
FIG. 25 is a perspective view of the instrument assembly of FIG. 5 (with the implant assembly also shown) and being used to implant the implant assembly in a femur according to the present disclosure, with the femur and the implant assembly being shown removed from the body of a patient P for clarity of viewing (note that the bone plate and fastener guide are shown in an unseated state)
Figure 26:
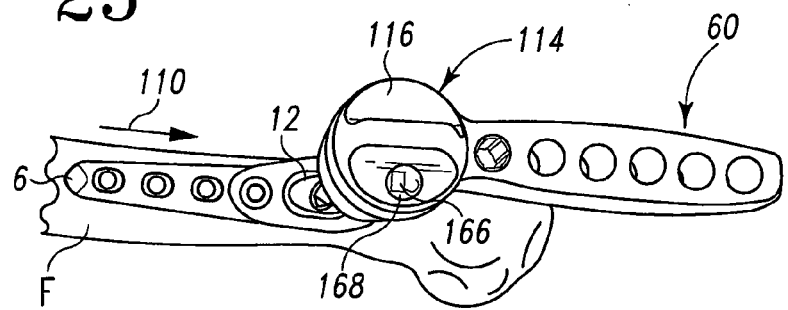
FIG. 26 is another perspective view of the instrument assembly of FIG. 5 (with the implant assembly also shown) and being used to implant the implant assembly in a femur according to the present disclosure, with the femur and the implant assembly being shown removed from the body of a patient P for clarity of viewing (note that the bone plate and fastener guide are shown in a seated state) (also note that the knob 116 is shown in a first position in which the "unlocked" icon is displayed)

After the lag screw assembly 4 is secured within a femoral head, neck, and shaft of the femur F of the patient P as shown in FIG. 4, a surgeon manipulates the plate holder 40 (with the bone plate 6 attached thereto) so that the bone plate 6 is advanced through the incision I to a position on the femur F that is spaced apart from the lag screw assembly 4 as shown in FIG. 25. Thereafter, the plate holder 40 is further manipulated to advance the bone plate 6 in the direction of arrow 110 to a position on the femur F in which the seating surface SS1 of the fastener guide 12 is positioned in contact with the seating surface SS2 of the bone plate 6 as shown in FIG. 26. (See also FIG. 1 showing the bone plate 6 seated against the fastener guide 12.) During such advancement of the bone plate 6 in the direction of arrow 110, the fastener guide 12 is advanced through the access opening 29 defined in the bone plate 6. Further, during such advancement of the bone plate 6 in the direction of arrow 110, the projection 26 of the bone plate 6 is mated with the channel 24 of the fastener guide 12. When the seating surface SS2 of the bone plate 6 is positioned in contact with the seating surface SS1 of the fastener guide 12, the bone plate and the fastener guide are in a seated state (shown in FIG. 26). In contrast, when the seating surface SS2 of the bone plate 6 is spaced apart from the seating surface SS1 of the fastener guide 12, the bone plate and the fastener guide are in an unseated state (shown in FIG. 25).

The instrument assembly 30 is operable to verify whether the bone plate 6 and the fastener guide 12 are in a seated state (i.e. the seating surface SS1 of the fastener guide 12 is located in contact with a seating surface SS2 of the bone plate 6) when the bone plate 6 is attached to the plate holder 40 as shown in FIG. 26. In particular, the instrument assembly 30 includes a stop structure 112 that is movable in relation to the body 42 of the plate holder 40 between an upper position (shown in FIG. 8) and a lower position (shown in FIG. 27). The instrument assembly 30 also includes an actuator 114 that is movable between a first position shown in FIG. 26 to a second position shown in FIG. 28. The actuator 114 includes a knob 116, a shaft 118, a cam 120, and a fastener 122 as shown in FIGS. 8 and 29. The shaft 118 is attached to the knob 116 since the shaft 118 and the knob are integrally molded together as one part. The cam 120 is attached to a distal end of the shaft 118 by the fastener 122. In particular, the cam 120 includes a central passage in which the distal portion of the shaft 118 is positioned. The distal portion of the shaft 118 includes an internally threaded recess. The fastener 122 is threadingly received within the internally threaded recess of the shaft 118 to secure the cam 120 to the shaft 118. When the instrument assembly 30 is assembled as shown in FIG. 8, rotation of the knob 116 causes rotation of the cam 120.

Figure 29:
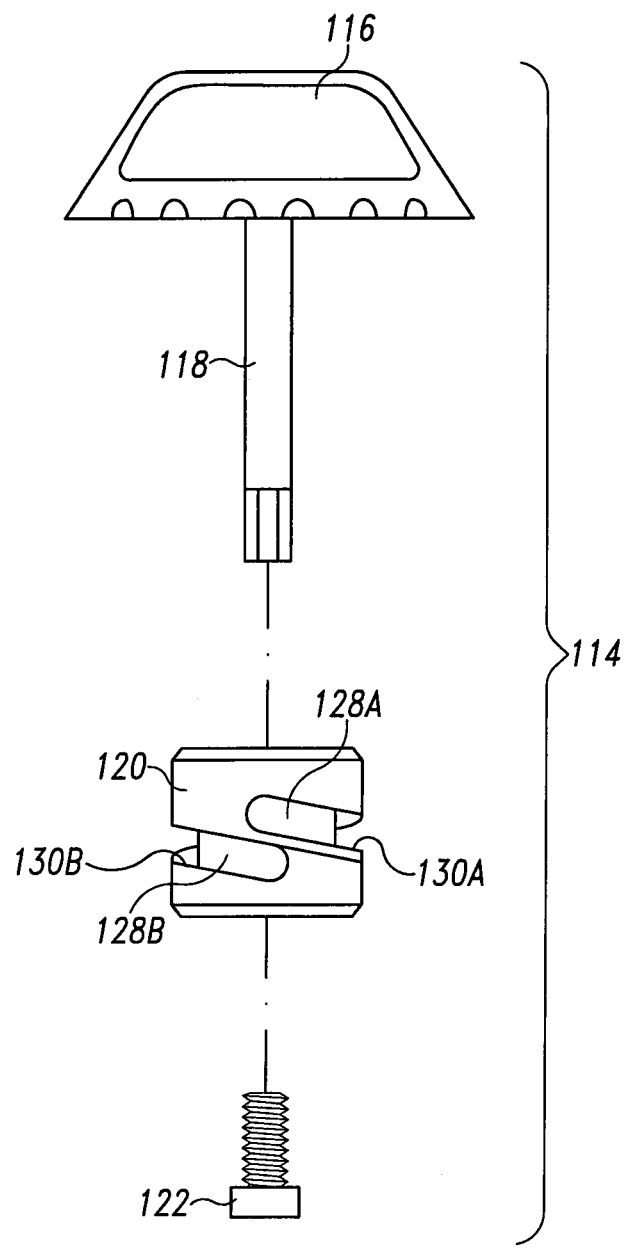
FIG. 29 is an exploded, perspective view of the actuator of the instrument assembly of FIG. 5.
Figure 30:
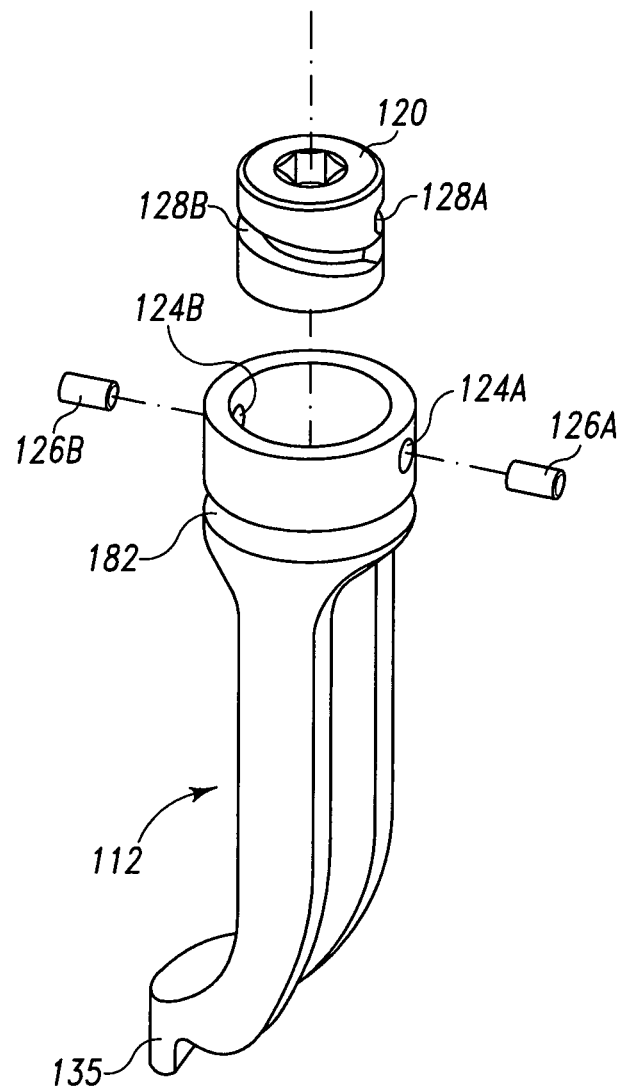
FIG. 30 is an exploded, perspective view of the cam, cam riders, and stop structure of the instrument assembly of FIG. 5.

The stop structure 112 has defined therein a number of holes 124A, 124B as shown in FIG. 30. The stop structure 112 further includes a number of cam riders 126A, 126B each being secured within a respective hole 124A, 124B, yet partially projecting from the respective hole 124A, 124B as shown in FIG. 8. The cam 120 has defined therein a cam track 128A and a cam track 128B. The cam track 128A defines a cam surface 130A, while the cam track 128B defines a cam surface 130B as shown in FIG. 29. When the instrument assembly 30 is assembled, the cam rider 126A is positioned within the cam track 128A and contacts the cam surface 130A, while the cam rider 126B is positioned within the cam track 128B and contacts the cam surface 130B. Rotation of knob 116 causes rotation of the cam 120. In turn, rotation of the cam 120 causes movement of the stop structure 112 in the direction of the axis X due to the interaction between the cam riders 126A, 126B and the cam surfaces 130A, 130B. Rotation of the knob 116 in a clockwise direction causes the stop structure 112 to move downwardly in a path of movement in the direction of the axis X, while rotation of the knob 116 in a counter-clockwise direction causes the stop structure 112 to move upwardly in the path of movement in the direction of the axis X. (See FIG. 8.)

The stop structure 112 includes a tang 135 located at the distal portion thereof. Downward movement of the stop structure 112 in its path of movement from its upper position (shown in FIG. 8) to its lower position (shown in FIG. 27), causes downward movement of the tang 135 from its upper position (shown in solid in FIG. 8) to its lower position (shown in FIG. 27). Note the phantom depiction of the tang 135 in FIG. 8 also shows the tang 135 at its lower position.

It should be appreciated that if the bone plate 6 and the fastener guide 12 were positioned in an unseated state as shown in FIG. 25, downward movement of the stop structure 112 would be prevented due to the presence of the fastener guide 12 in the path of movement of the tang 135 of the stop structure 112. Indeed, the fastener guide 12 would block the downward movement of the stop structure. Thus, if a surgeon is attempting to rotate the knob 116 from its first position (shown in FIG. 26) to its second position (shown in FIG. 28) and rotation of the knob 116 is prevented at some point therebetween, the surgeon would have positive verification that the bone plate 6 and the fastener guide 12 are in an unseated state.

On the other hand, if the bone plate 6 and the fastener guide 12 were positioned in a seated state as shown in FIG. 26, downward movement of the stop structure 112 would be allowed due to the lack of presence of the fastener guide 12 in the path of movement of the tang 135 of the stop structure. Indeed, the fastener guide 12 would not block the downward movement of the stop structure 112 since the fastener guide 12 would be spaced apart from the path of movement of the tang 135. Thus, if a surgeon rotates the knob 116 from its first position (shown in FIG. 26) to its second position (shown in FIG. 28) without complication, the surgeon would have positive verification that the bone plate 6 and the fastener guide 12 are in a seated state.

The knob 116 is rotatable about the axis X as shown in FIG. 8. Rotation of the knob 116 from its first position (shown in FIG. 26) 180° about the axis X to its second position (shown in FIG. 28) causes the stop structure 112 to move from its upper position (shown in FIG. 8) to its lower position (shown in FIG. 27).

Note that after the stop structure 112 is moved to its lower position (shown in FIG. 27), the tang 135 prevents movement of the bone plate 6 in relation to the fastener guide 12. Thus, the stop structure 112 locks the bone plate 6 and the fastener guide 12 in its seated state when the stop structure 112 is positioned in its lower position (shown in FIG. 27).

Figure 28:
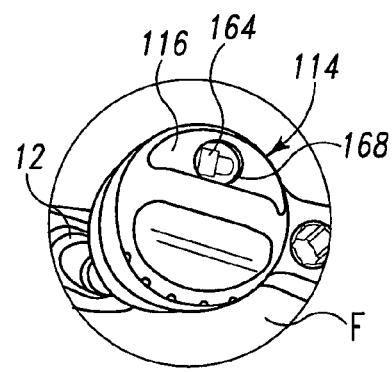
FIG. 28 is an enlarged, fragmentary, perspective view of the instrument assembly of FIG. 5 showing the knob 116 in a second position in which the "locked" icon is displayed.
Figure 31:
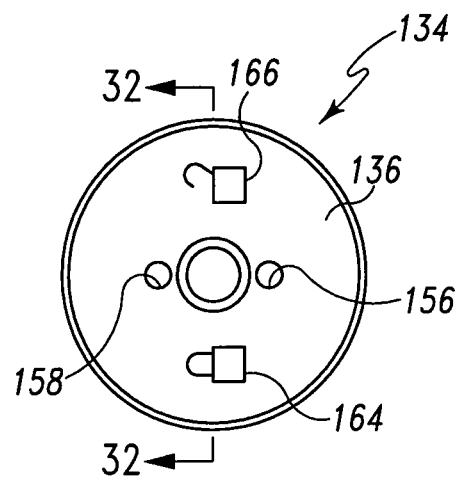
FIG. 31 is a top elevational view of the support member of the instrument assembly of FIG. 5.
Figure 32:
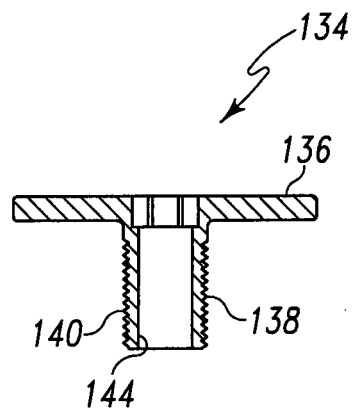
FIG. 32 is a cross sectional view of the support member taken along the line 32-32 of FIG. 31.

The instrument assembly 30 is configured to generate a tactile and audible indication of when the stop structure 112 is located at its upper position (shown in FIG. 26) and at its lower position (shown in FIG. 28). In particular, the instrument assembly 30 further includes a support member 134 that includes an upper portion 136 and a lower portion 138 as shown in FIGS. 31-32. (See also FIG. 8.) The lower portion 138 includes a set of external threads 140 that mate with a set of internal thread 142 defined in the neck 43 of the plate holder 40 as shown in FIG. 8. The support member 134 defines a passage 144 through which the shaft 118 of the actuator 114 extends. A sleeve 146 is positioned within the cavity 66 and surrounds both the neck 43 of the plate holder 40 and the lower portion 138 of the support member 134 as shown in FIG. 8.

Figure 33:
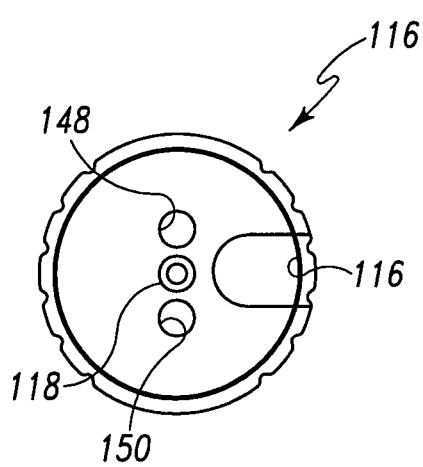
FIG. 33 is a bottom elevational view of the knob of the actuator of FIG. 29.
Figure 34:
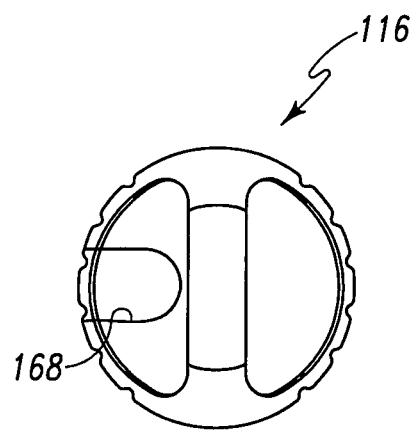
FIG. 34 is a top elevational view of the knob of the actuator of FIG. 29.

The knob 116 includes a spring recess 148 and a spring recess 150 as shown in FIGS. 33-34. A spring 152 is positioned in the spring recess 148, while a spring 154 is positioned in the spring recess 150. (See FIG. 5.) The upper portion 138 of the support member 134 has defined therein a detent recess 156 and a detent recess 158 as shown in FIGS. 31-32.

When the knob 116 is positioned in its first position (shown in FIG. 26), a ball detent 160 is interposed between the spring 152 and the detent recess 156 thereby resulting in the ball detent 160 being urged into the detent recess 156 as shown in FIG. 8. Similarly, when the knob 116 is positioned in its first position (shown in FIG. 26), a ball detent 162 is interposed between the spring 154 and the detent recess 158 thereby resulting in the ball detent 162 being urged into the detent recess 158 as shown in FIG. 8.

While the knob 116 is being rotated from its first position (shown in FIG. 26) to its second position (shown in FIG. 28), the ball detent 160 is advanced out of the detent recess 156 and is interposed between the spring 152 and the support member 134. Similarly, while the knob 116 is being rotated from its first position (shown in FIG. 26) to its second position (shown in FIG. 28), the ball detent 162 is advanced out of the detent recess 158 and is interposed between the spring 154 and the support member 134.

Then, when the knob 116 arrives so as to be positioned at its second position (shown in FIG. 28), the ball detent 160 becomes interposed between the spring 152 and the detent recess 158 thereby resulting in the ball detent 160 being urged into the detent recess 158. Similarly, when the knob 116 is positioned at its second position (shown in FIG. 26), the ball detent 162 becomes interposed between the spring 154 and the detent recess 156 thereby resulting in the ball detent 162 being urged into the detent recess 156.

Figure 27:
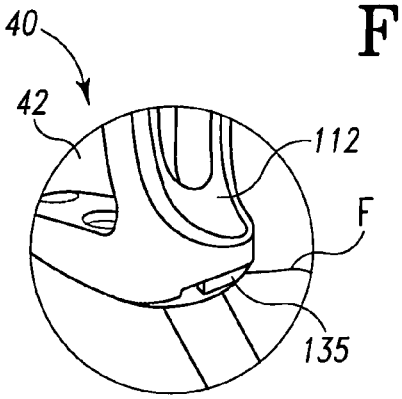
FIG. 27 is an enlarged, fragmentary, perspective view of the instrument assembly of FIG. 5, however, the stop structure 112 is shown positioned in its lower position.

When the knob 116 arrives so as to be positioned at its second position (shown in FIG. 28), a click sound is heard by the surgeon indicating that the stop structure 112 is now positioned at its lower position shown in FIG. 27. Similarly, when the surgeon rotates the knob 116 back to its first position (shown in FIG. 26) from its second position (shown in FIG. 28), arrival of the knob 116 at its first position (shown in FIG. 26) results in a similar click sound being heard by the surgeon. The click sounds are caused by the ball detents 160, 162 being urged into their respective detent recesses 156, 158 by their respective springs 152, 154.

In addition, the instrument assembly 30 is configured to provide a visual indication of when the stop structure 112 is located at its upper position (shown in FIG. 26) and at its lower position (shown in FIG. 28). In particular, the support member 134 includes a "locked" icon 164 and an "unlocked" icon 166 located on an upper surface of the upper portion 136 of the support member 134 as shown in FIG. 31. (See also FIG. 6.) The icons 164, 166 are preferably etched into an upper surface of the upper portion 136 of the support member 134. The icon 164 is preferably colored red, while the icon 166 is preferably colored green. Of course, other color schemes may be used. The knob 116 has defined therein a viewing opening 168 as shown in FIGS. 33-34. As shown in FIG. 26, when the knob 116 is positioned in its first position, the viewing opening 168 is positioned over the "unlocked" icon 166 thereby displaying the "unlocked" icon to the surgeon which informs the surgeon the stop structure 112 is now positioned at its upper position. On the other hand, as shown in FIG. 28, when the knob 116 is positioned in its second position, the viewing opening 168 is positioned over the "locked" icon 164 thereby displaying the "locked" icon to the surgeon which informs the surgeon the stop structure 112 is now positioned at its lower position.

Furthermore, the instrument assembly 30 is configured to provide an additional visual indication of when the stop structure 112 is located at its upper position (shown in FIG. 26) and at its lower position (shown in FIG. 28). In particular, the body 42 of the plate holder 40 has defined therein a number of viewing holes 180 as shown in FIGS. 9-10. The stop structure 112 defines a groove 182 that extends in a circumferential manner around the stop structure as shown in FIG. 30. The groove 182 is preferably colored red. Of course, the groove may be colored with a color other than red, such as yellow, pink, or orange. When the stop structure 112 is located at its upper position (shown in FIG. 26), the red-colored groove 182 of the stop structure 112 is hidden from view of a user of the instrument assembly 30 since the red-colored groove 182 is (i) located within the neck 43 of the body 42 of the plate holder 40, and (ii) located proximal to the viewing opening 180 defined in the body 42 of the plate holder 40. (See, e.g., FIG. 8, as well as, FIG. 7.) In contrast, when the stop structure 112 is located at its lower position (shown in FIG. 28), the red-colored groove 182 of the stop structure 112 is exposed to a user of the instrument assembly 30 since the red-colored groove is (i) located distal to the neck 43 of the body 42 of the plate holder 40, and (ii) aligned with the viewing openings 180 defined in the body 42 of the plate holder 40. (See, e.g., FIGS. 7 and 8.)

Thus, when the knob 116 is positioned in its first position as shown in FIGS. 8 and 26, the red-colored groove 182 is hidden from view thereby informing the surgeon the stop structure 112 is now positioned at its upper position. On the other hand, as shown in FIG. 28, when the knob 116 is positioned in its second position, the red-colored groove 182 is exposed to a user of the instrument assembly 30 which informs the surgeon the stop structure 112 is now positioned at its lower position.

Use of Instrumentation and Implant Components

Figure 35:
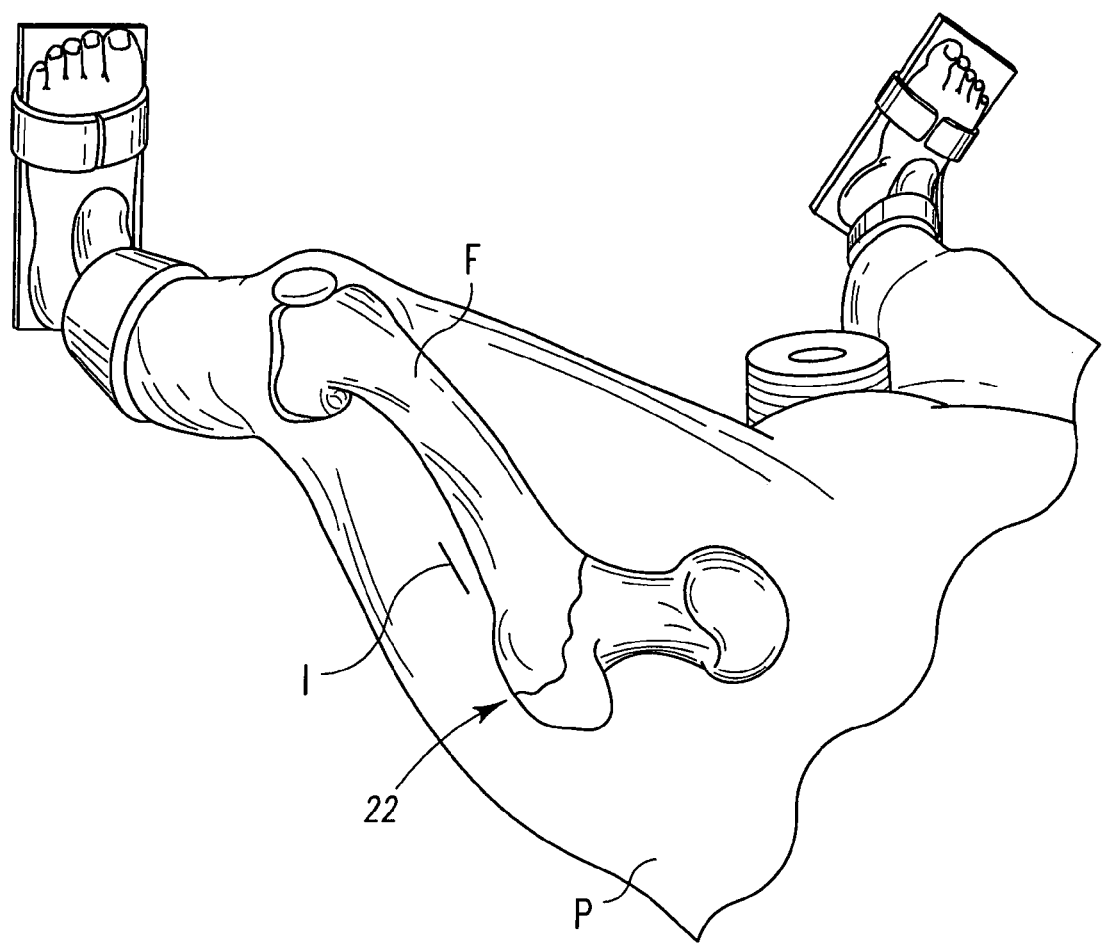
FIG. 35 is a fragmentary, perspective view of a patient with a fractured femur.

Use of the instrumentation and implant components described above facilitate reduction of a hip fracture in a minimally invasive manner. In particular, in order to perform such a procedure, a patient P is placed in a supine position on a standard fracture table. The fracture is then reduced and aligned using traction with external rotation followed by approximately 20 degrees of internal rotation to compress the fracture 22 (see FIG. 35). The reduction is then verified using dual-plane image intensification. The hip is then prepared and draped in a conventional manner.

Thereafter, an incision I is made that is 3-8 cm long (depending on the length of the bone plate being used) in the lateral aspect of the hip, with dissection beginning distal to the flare of the greater trochanter down to the vastus ridge and extending distally. (See FIG. 35.) The dissection is carried sharply down through the skin and subcutaneous tissue to the fascia lata. The fascia lata is split longitudinally thereby exposing the vastus lateralis. The vastus lateralis is then retracted anteriorly and the lateral aspect of the femoral shaft is then exposed.

Figure 60:
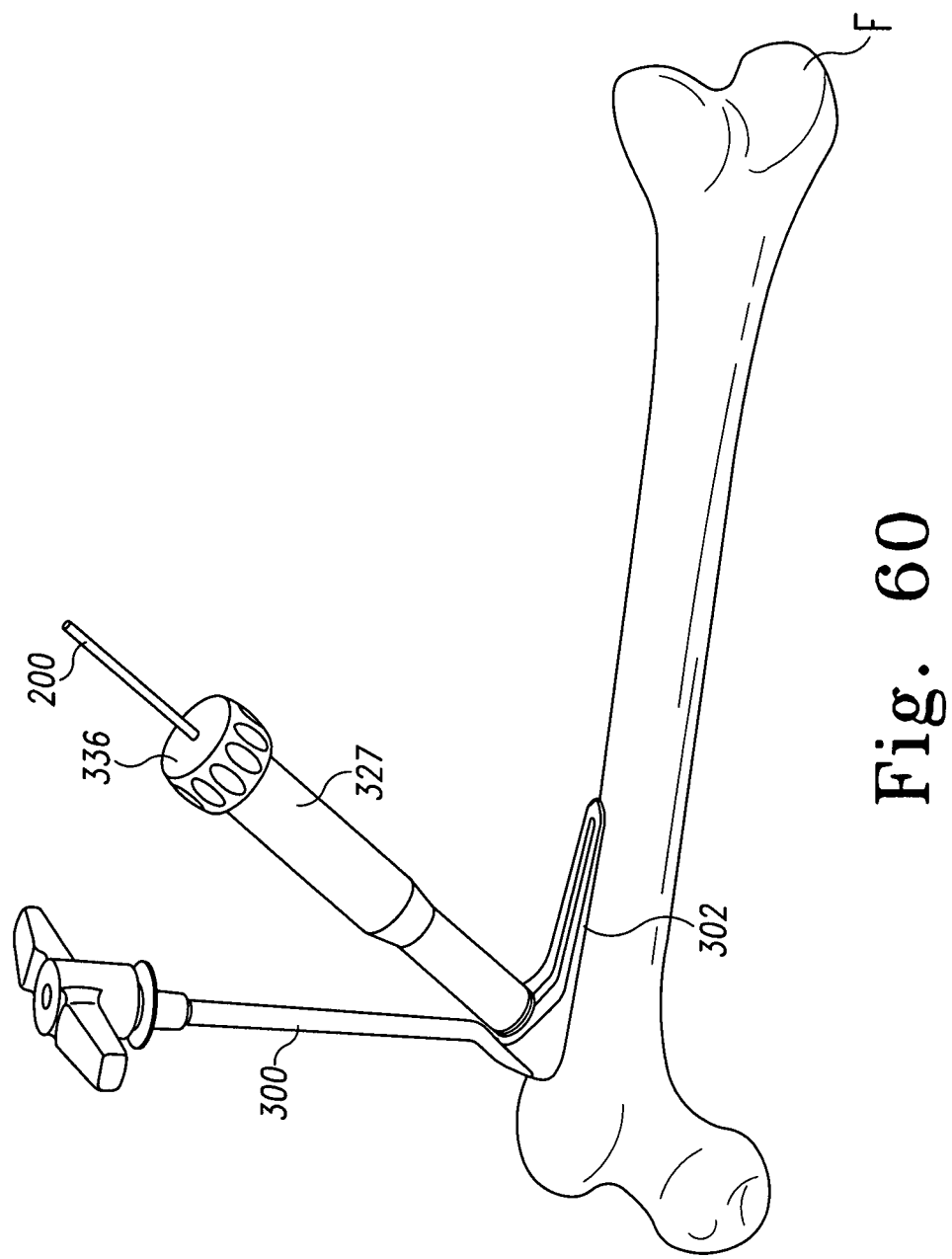
FIGS. 60 and 61 are perspective views of the guide component of FIG. 39, the sheath of FIG. 44, and the sheath of FIG. 47 being arranged in an assembled state and being used to place the guide wire of FIG. 37 in a femur of a patient in a minimally invasive manner according to the present disclosure.
Figure 61:
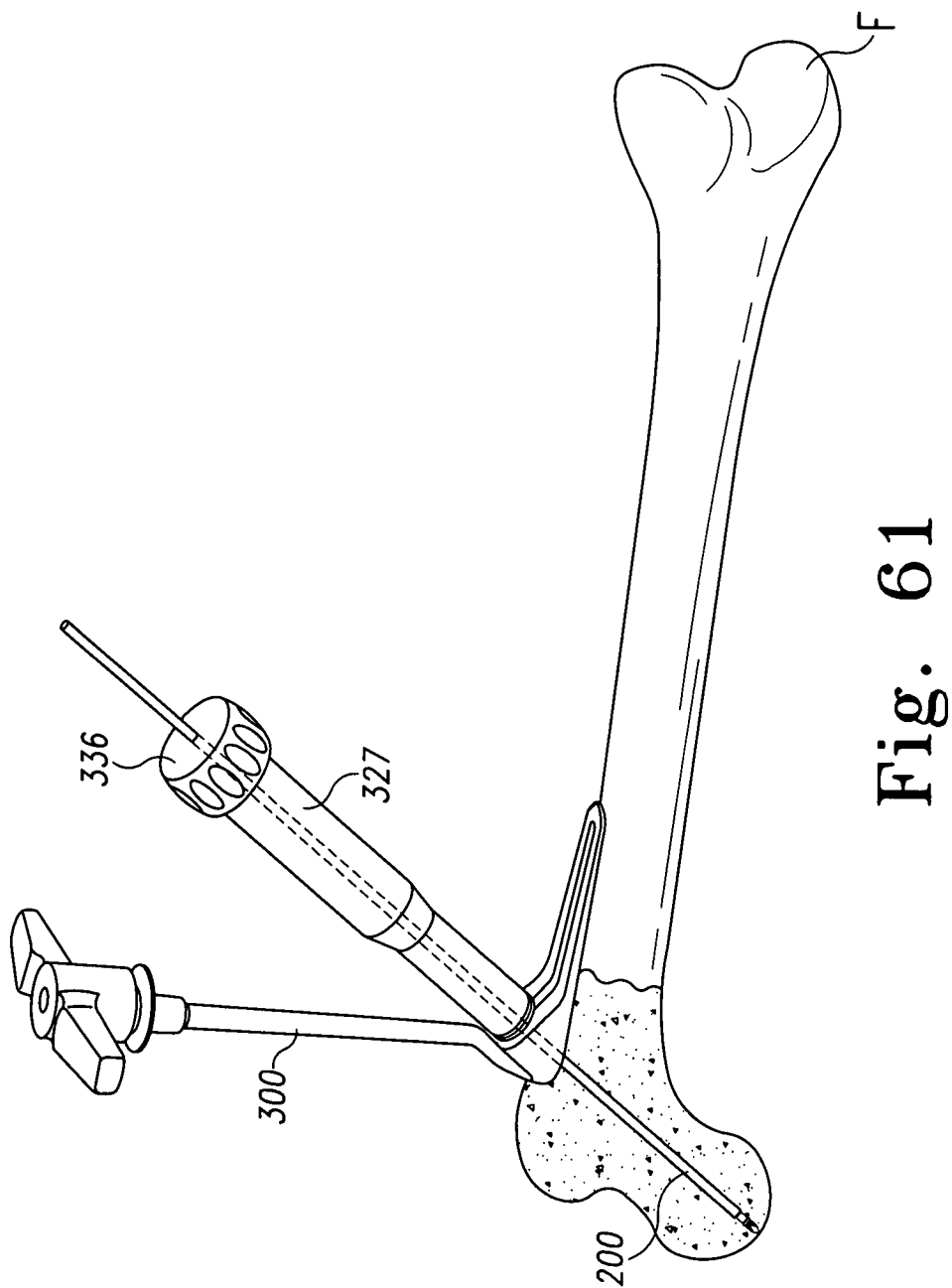
Figure 62:
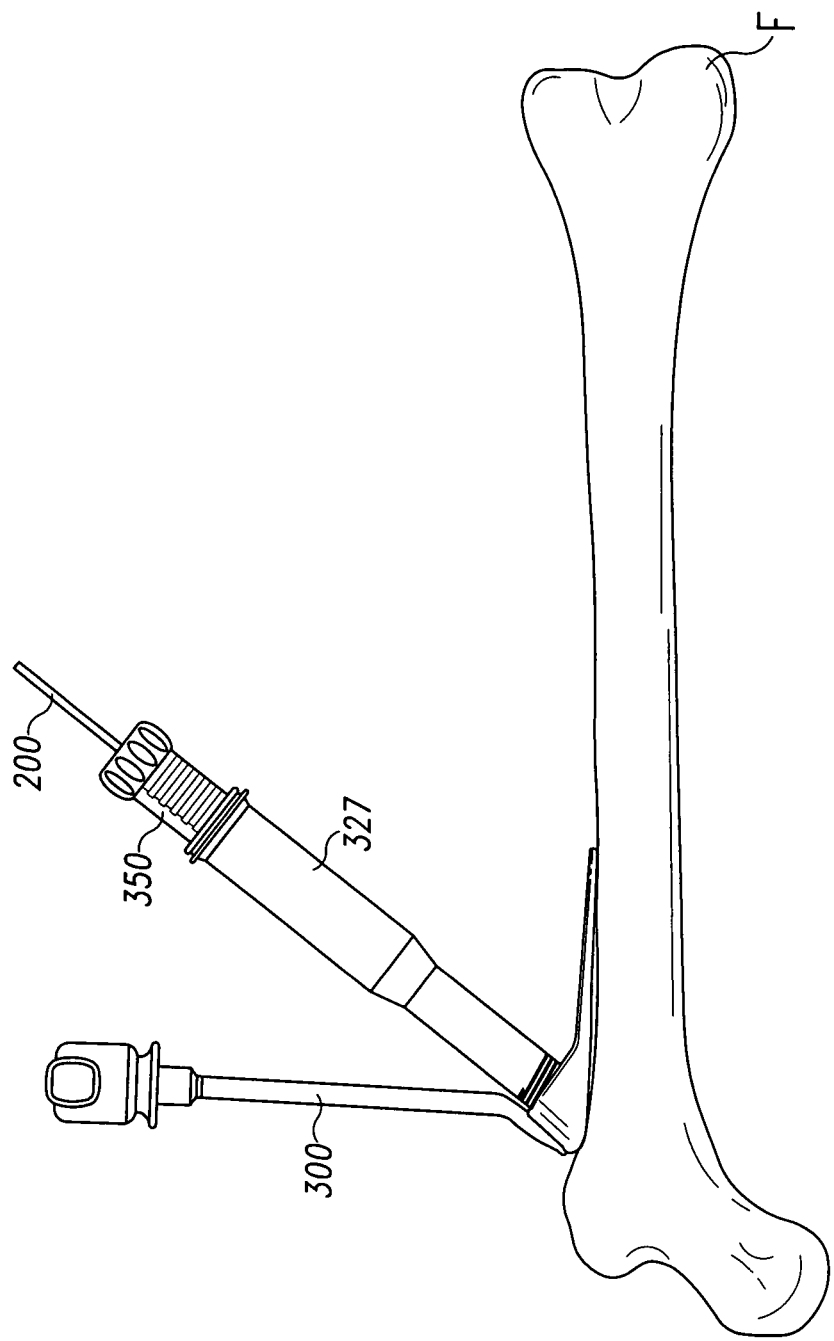
FIGS. 62 and 63 are perspective views of the guide component of FIG. 39, the sheath of FIG. 44, and the stop structure of FIG. 47 being arranged in an assembled state according to the present disclosure.
Figure 63:
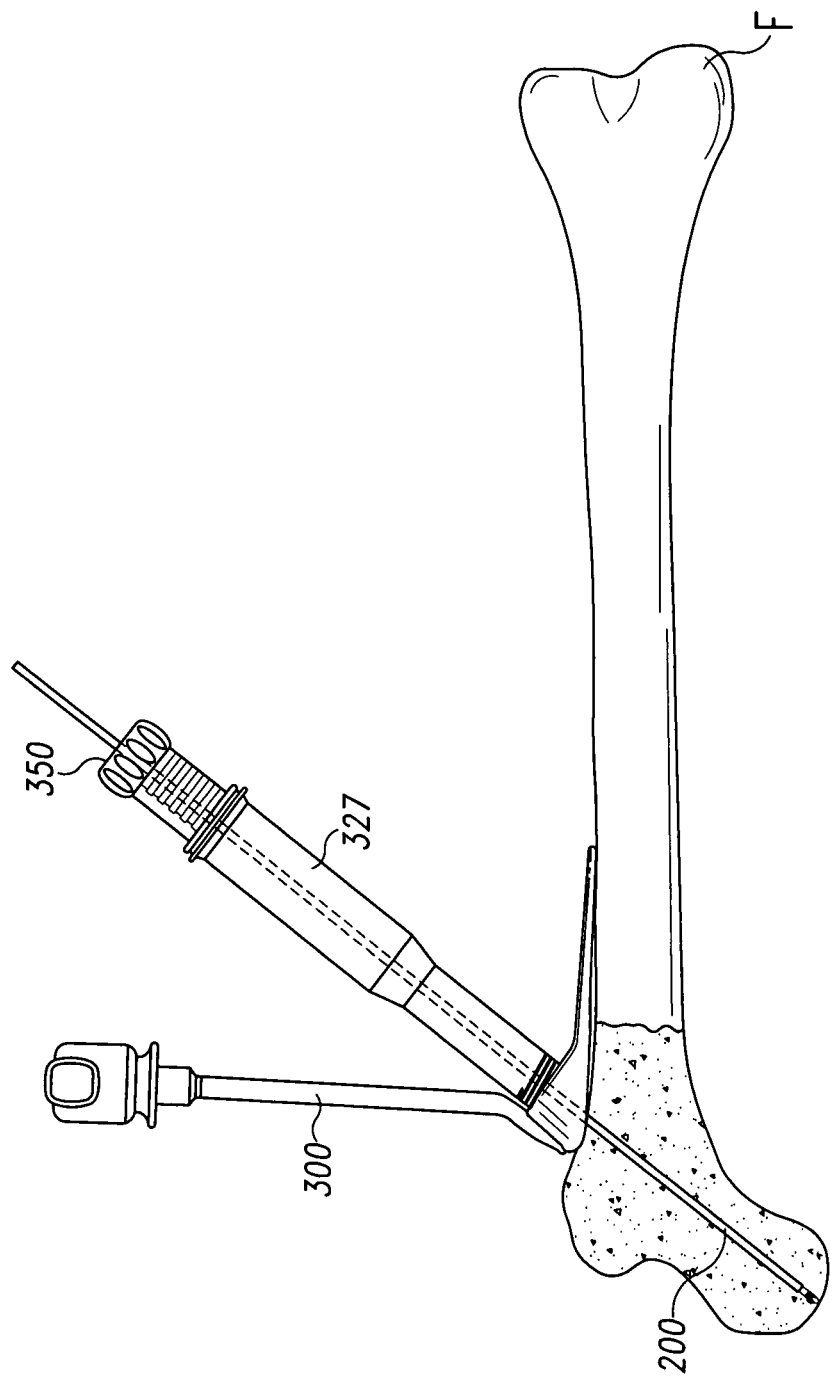

The guide wire 200 is exteriorly placed adjacent to the femoral neck to assess lateral positioning and neck angle. After the surgeon measures or otherwise determines the neck angle of the femur F, the guide wire 200 is then advanced into the shaft, neck, and head of the femur F of the patient P. The surgeon may choose to advance the guide wire into the femur "freehand" (i.e. without the aid of a guiding structure). Alternatively, the surgeon may choose to advance the guide wire into the femur with the aid of the guide component 300 and associated instruments. If the latter approach is chosen, the surgeon selects one of various guide components 300 located within an instrumentation and implant kit (not shown) which has an angle A that best matches the neck angle of the femur. The selected guide component 300 is then advanced so as to be positioned in contact with the femur F. This is accomplished by manipulating the guide component 300 through the incision I (See FIG. 4) and then subsequently positioning the guide component appropriately on the femur. (See, e.g., the position of the base 302 on the femur F in FIGS. 60-61.) Thereafter, the distal portion of the sheath 327 is passed through the incision I and attached to the guide component 300. (See also, e.g. FIGS. 60-61.) The sheath 327 is attached to the guide component 300 by meshingly engaging the set of external threads 332 of the sheath with the set of internal threads 310 of the base 302 of the guide component 300. Then, the sheath 336 is advanced into the passageway 328 of the sheath 327 as shown in FIGS. 60-61. Since the angle A defined by the base 302 of the guide component substantially matches the neck angle of the femur, advancement of the guide wire 200 through the passageway 338 of the sheath 336 will properly place the guide wire 200 into the shaft, neck, and head of the femur F. Thus, the guide wire 200 is then advanced through the passageway 338 of the sheath 336 into the shaft, neck, and head of the femur F as shown in FIGS. 60-61. Thereafter, the sheath 336 is removed from the passageway 328 of the sheath 327 over the guide wire 200, thereby leaving the guide wire in place.

Alternatively, if the surgeon advanced the guide wire 200 into the shaft, neck, and head of the femur F freehand, the guide component 300 (without the sheath 327 attached thereto) would then need to be positioned in contact with the femur. To this end, the guide component 300 would be manipulated through the incision I and then subsequently positioned on the femur as shown in FIG. 60-61 while the guide wire 200 is extending through the base 302. Thereafter, the sheath 327 would be advanced over the guide wire and attached to the guide component by coupling the coupling component 330 of the sheath 327 to the coupling component 308 of the guide component 300.

At this point in the procedure, regardless of the approach used to place the guide wire in the femur, the guide component 300 is positioned in contact with the femur with the guide wire 200 extending through (i) the passageway 306 of the base 302 of the guide component, and (ii) the passageway 328 of the sheath 327. Thereafter, the stop structure 350 is advanced over the guide wire 200 and into the passageway 328 of the sheath 327 and then manipulated so as to secure the stop structure 350 in fixed in relation to the sheath 327. To this end, the stop structure 350 is passed over the guide wire 200 so that the guide wire extends through the central passage 352. As the stop structure 350 is further advanced and approaches the proximal end of the sheath 327, the pair of flat exterior surface portions 364 is aligned with the key members 358. While the flat exterior surface portions 364 are aligned with the key members 358, the stop structure is further advanced thereby causing the distal portion of the stop structure to advance into the proximal portion of the passageway 328 of the sheath 327. Thereafter, the stop structure 350 is rotated so as to cause the pair of flat exterior surface portions 362 to align with the key members 358. While the flat exterior surface portions 362 are aligned with the key members 358, the stop structure is further advanced thereby causing the stop structure to further advance into the passageway 328 of the sheath 327 until the proximal surface 382 of the stop structure becomes aligned with a stop mark 400 (see FIGS. 37 and 54) located on the guide wire 200. The stop mark 400 on the guide wire 200 is defined by a transition between the black color located on the proximal portion 206 of the body 204 of the guide wire 200 and the metallic gray or silver intermediate portion of the guide wire juxtaposed to the black proximal portion 206. After the proximal surface 382 becomes aligned with the stop mark 400, the stop structure is rotated in relation to the sheath 327 whereby the key members 358 are respectively advanced into keyways 356 as shown in FIG. 54. So positioned, the stop structure 350 is fixed in relation to the sheath 327 whereby axial movement of the stop structure in relation to the sheath 327 is prevented. Note that, as shown in FIG. 54, the keyways 356 in which the key members 358 are respectively positioned have indicia markings "105" associated therewith. Thus, a surgeon is informed that the proper length of a lag screw assembly 4 which is to be implanted in the femur is 105 mm.

Figure 64:
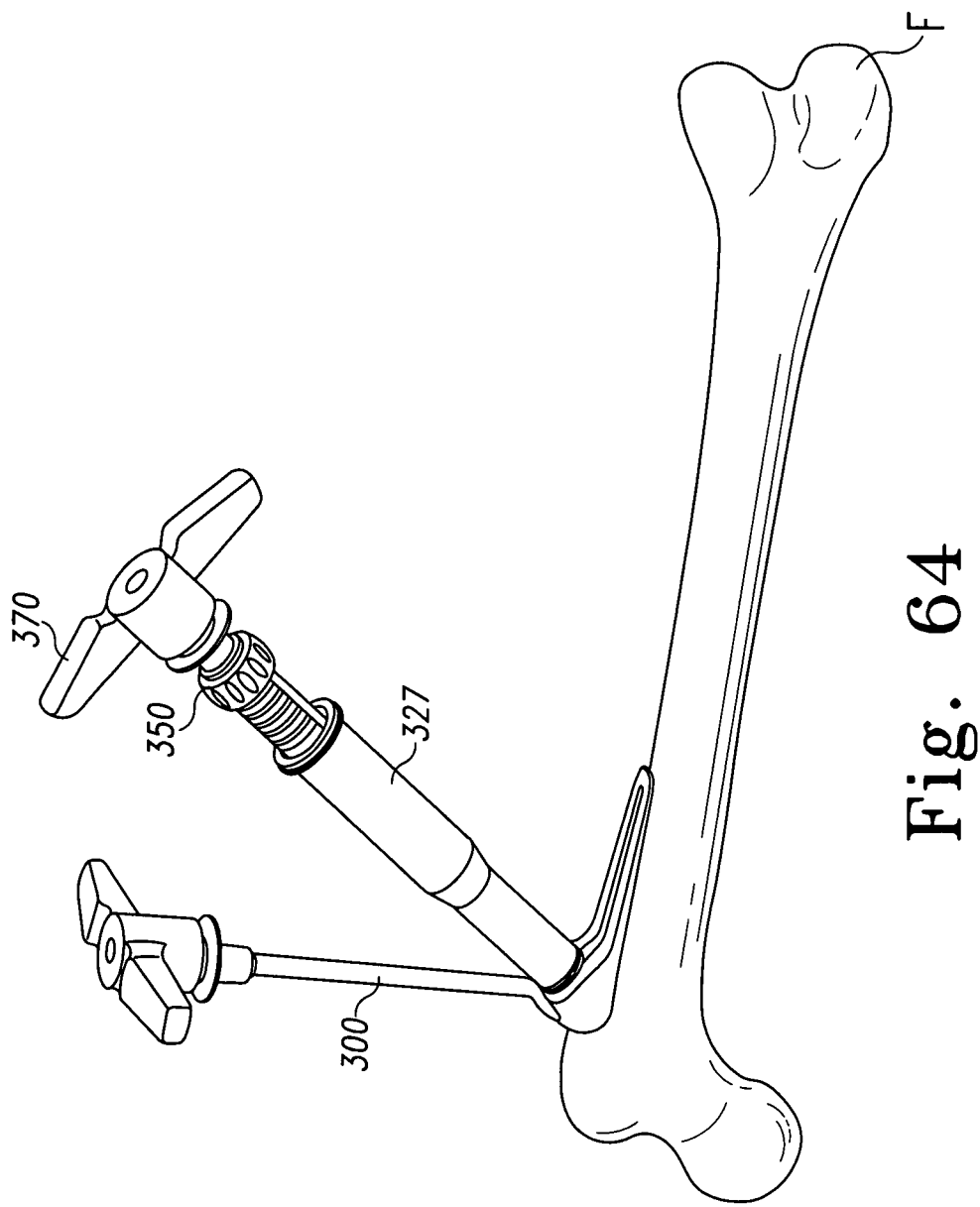
FIGS. 64 and 65 are perspective views of the guide component of FIG. 39, the sheath of FIG. 44, the stop structure of FIG. 47, and the drill of FIG. 55 being arranged in an assembled state and being used to prepare a fastener cavity in a femur of a patient in a minimally invasive manner according to the present disclosure (note that FIG. 65 shows the drill with its handle removed)
Figure 65:
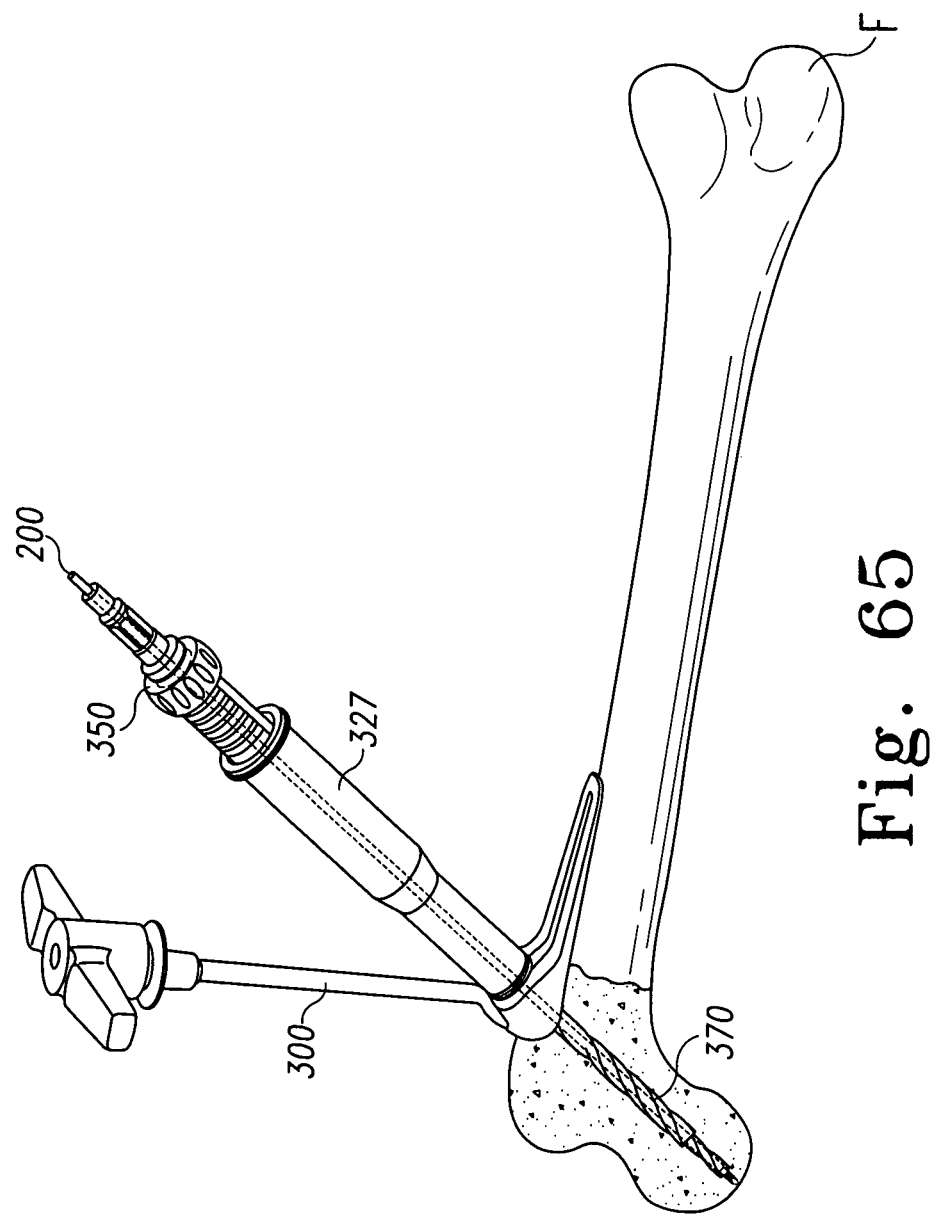

Next, the cannulated drill 370 is advanced over the guide wire 200 so that the guide wire is positioned in the passageway 372. As shown in FIGS. 64-65, the drill 370 is further advanced over the guide wire 200 so as to position the drill 370 in the central passage 352 of the stop structure 350 while the stop structure is axially fixed in relation to the sheath 327. As the drill 370 is further advanced, the cutting surface 376 of the drill creates a fastener cavity in the femur as shown in FIG. 65. With further advancement of the drill 370 through the central passage 352, the shoulder 380 of the drill 370 comes into contact with the proximal surface 382 of the stop structure 350 as shown in FIG. 64. Contact between the shoulder 380 of the drill and the proximal surface 382 of the stop structure prevents further advancement of the drill within the central passage 352 of the stop structure, thereby limiting further penetration of the drill 370 into the femur F. Thereafter, the drill 370 is removed from the sheath 327 over the guide wire 200.

Figure 66:
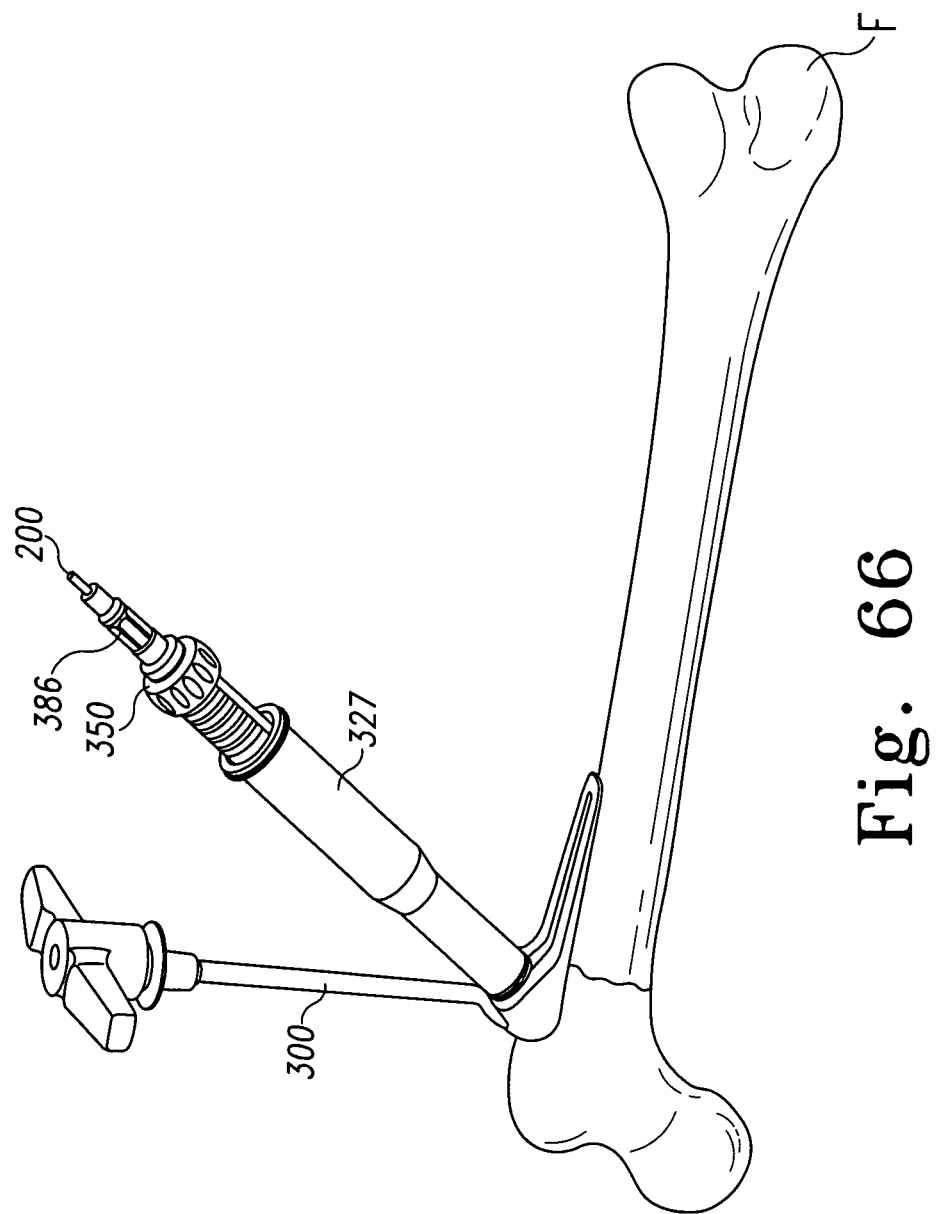
FIGS. 66 and 67 are perspective views of the guide component of FIG. 39, the sheath of FIG. 44, the stop structure of FIG. 47, and the tap of FIG. 57 being arranged in an assembled state and being used to prepare a fastener cavity in a femur of a patient in a minimally invasive manner according to the present disclosure (note that FIG. 66 shows the tap with its handle removed).
Figure 67:
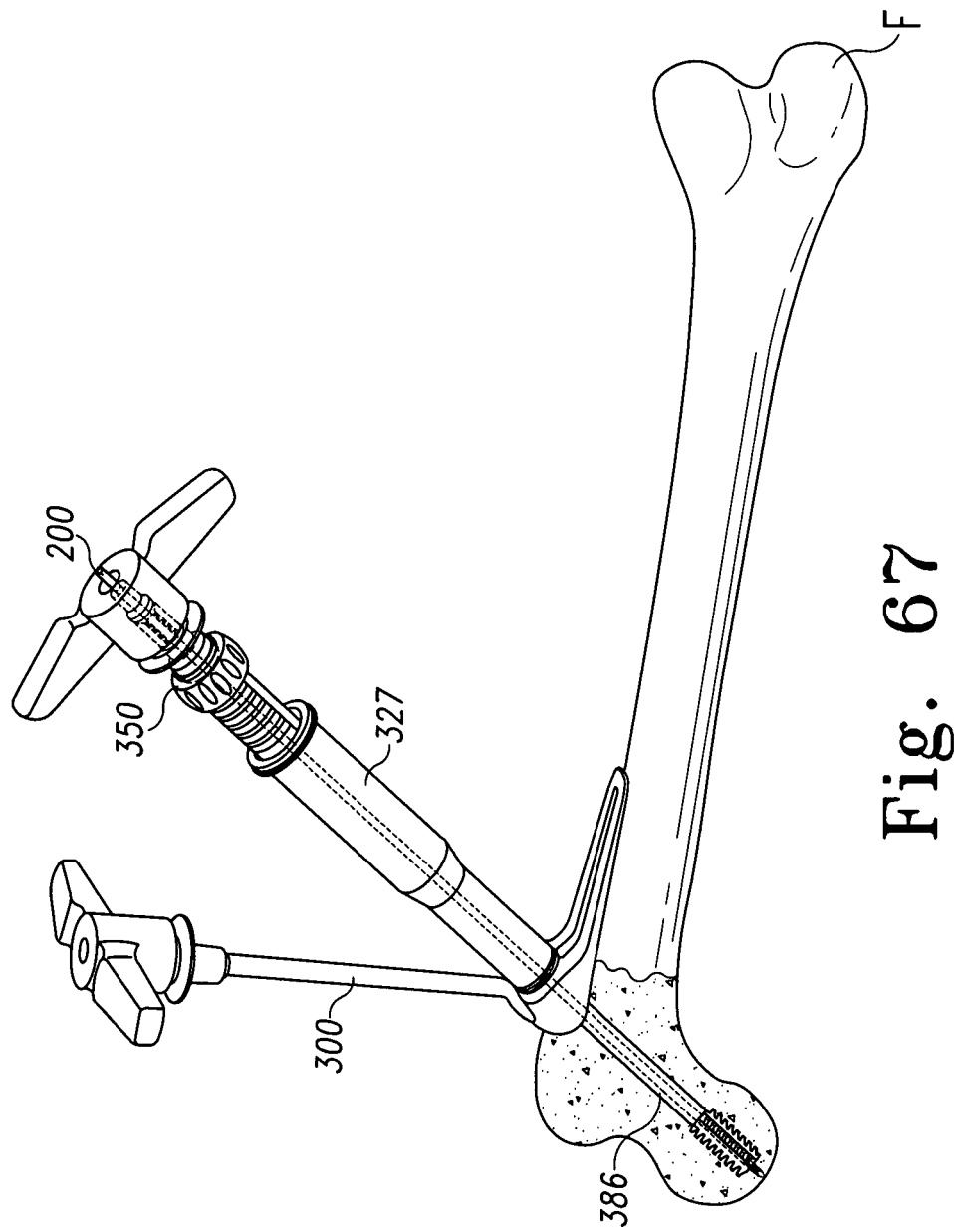

Then, the cannulated tap 386 may be advanced over the guide wire 200 and into the fastener cavity to create female (internal) screw threads in the internal walls defining the fastener cavity to prepare the fastener cavity for receipt of the lag screw assembly 4 as shown in FIGS. 66-67. To this end, the tap 386 is advanced over the guide wire 200 so that the guide wire is positioned in the passageway 388. The tap 386 is further advanced over the guide wire 200 so as to position the tap 386 in the central passage 352 of the stop structure 350 while the stop structure is axially fixed in relation to the sheath 327. As the tap 386 is further advanced, the cutting surface 392 of the tap creates female (internal) screw threads in the internal walls defining the fastener cavity as shown in FIG. 67. With further advancement of the tap 386 through the central passage 352, the shoulder 396 of the tap 386 comes into contact with a proximal surface 382 of the stop structure 350. Contact between the shoulder 396 of the tap and the proximal surface 382 of the stop structure prevents further advancement of the tap within the central passage 352 of the stop structure, thereby limiting further penetration of the tap 386 into the femur F. Thereafter, the tap 386 is removed from the sheath 327 over the guide wire 200. Then, the sheath 327 is decoupled from the guide component 300 and removed over the guide wire 200 from the patient's body. Then, the guide component 300 is removed over the guide wire from the patient's body through the incision I, thereby leaving the guide wire in place.

The lag screw assembly 4 is then advanced into the fastener cavity with the lag screw component 14 being advanced over the guide wire 200. The guide wire is then removed from the patient's body through the incision I. The lag screw assembly 4 is secured to the femur F by rotating the lag screw 10 with a driver tool (not shown) until the lag screw assembly 4 assumes a position in relation to the femur F as shown in FIG. 4.

Once the lag screw assembly 4 has been secured within the femur as shown in FIG. 4, the bone plate 6 may be assembled to the fastener guide or barrel 12. This is accomplished with the assistance of the instrument assembly 30. In particular, using the instrument assembly 30 having the bone plate 6 attached thereto (as described above), the bone plate 6 is advanced through the incision I. After being advanced through the incision I, the bone plate 6 is advanced distally until the proximal end of the bone plate 6 is located distal to the lag screw assembly 4 as shown in FIG. 25. The bone plate 6 is then slid toward the lag screw assembly 4 so that the fastener guide 12 is passed through the access opening 29 defined in the proximal end of the bone plate 6. Also during sliding of the bone plate 6 toward the lag screw assembly 4, the projection 26 of the bone plate 6 advances into the channel 24 of the fastener guide 12. Continued advancement of the bone plate 6 in relation to the fastener guide 12 results in the seating surface SS1 of the fastener guide 12 contacting the seating surface SS2 of the bone plate 6 as shown in FIG. 26. When seating surface SS1 is in contact with the seating surface SS2, the bone plate 6 and the fastener guide 12 are in an assembled state.

During the above-described advancement of the bone plate 6 relative to the fastener guide 12, the stop structure 112 of the instrument assembly 30 is located in its upper position. When the stop structure 112 is in its upper position, the knob 116 of the actuator 114 of the instrument assembly 30 is located at its first position (shown in FIG. 26) such that the "unlocked" icon 166 is visible through the viewing opening 168 of the knob 116.

When the surgeon believes the bone plate 6 has been advanced into its assembled state with the fastener guide 12, the surgeon rotates the knob 116 clockwise so that the viewing opening 168 is moved to a second position (shown in FIG. 28) in which the viewing opening 168 is aligned with "locked" icon 164 thereby displaying the "locked" icon 164 through the viewing opening 168. If the knob 116 is prevented from moving to from its first position (shown in FIG. 26) to its second position (shown in FIG. 28), the surgeon is positively notified the bone plate 6 and the fastener guide 12 are not in an assembled state. Thus, the surgeon would need to further mate the bone plate 6 and the fastener guide 12 so that the seating surface SS1 of the fastener guide 12 is positioned in contact with the seating surface SS2 of the bone plate 6. On the other hand, if the knob 116 is allowed to move from its first position (shown in FIG. 26) to its second position (shown in FIG. 28), then a surgeon is positively notified the bone plate 6 and the fastener guide 12 are in their assembled state. When the knob 116 is positioned at its second position (shown in FIG. 28), the stop structure 112 is located at its lower position thereby retaining or locking the bone plate 6 and the fastener guide 12 in their assembled state.

If desired, prior to moving the knob 116 from its first position ("unlocked" icon displayed and red-colored groove 182 hidden from view) to its second position ("locked" icon displayed and red-colored groove 182 exposed to a user), the bone plate 6 may be impacted with an impactor 170 as shown in FIG. 17. In particular, the impactor 170 is manipulated until its distal end is received within an impactor recess 172 of the plate holder 40. Thereafter, the proximal end of the impactor 170 is tapped firmly several times (e.g. three or four) with a mallet (not shown) to transmit force to the bone plate 6 thereby ensuring the bone plate 6 and the lag screw assembly 4 are fully mated.

When the knob 116 is positioned at its second position (shown in FIG. 28), indicating that the bone plate 6 and the fastener guide 12 are in their assembled state, the guide component 60 is moved from its position shown in FIG. 17 to its position shown in FIG. 16. This is accomplished by moving the actuator 74 from its lower position (shown in solid in FIG. 8) to its upper position (shown in phantom in FIG. 8), and thereafter rotating the guide component 180° about the axis X (see FIG. 8) from its position shown in FIG. 17 to its position shown in FIG. 16. Upon arriving at its position shown in FIG. 16, the guide component 60 becomes locked in relation to plate holder 40. At this position, the guide holes 62, 62A of the guide component 60 are respectively aligned with the fastener openings 7, 7A of the bone plate 6.

With the guide component 60 secured in its position shown in FIG. 16 (see also FIG. 8), instruments such as the drill assembly 70 may be advanced through the guide holes 62, 62A and the fastener openings 7, 7A to create fastener cavities (not shown) in the femur that are aligned with the fastener openings 7, 7A. Thereafter, the bone screws 8A, 8B (such as 4.5 mm bone screws) are driven through the fastener openings 7, 7A of the bone plate 6 and into the shaft of the femur F. The bone screws 8A, 8B are driven (one at a time) through an outer sheath S that respectively extends through the guide holes 62, 62A in the guide component. (See, e.g., FIG. 8.)

After placement of the final bone screw 8A, 8B, the driver 68 is advanced through the guide hole 62A of the guide component 60 until the drive structure 96 of the tip portion 92 of the driver mates with drive structure 100 of the coupling component 44. Thereafter, the driver 68 is rotated in the counter-clockwise direction thereby causing the coupling component 44 to be rotated in relation to the bone plate 6. Rotation of the coupling component 44 in relation to the bone plate 6 in the counter-clockwise direction causes the set of external threads 52 of the coupling component 44 to become meshingly disengaged with the set of internal threads 54 of the bone plate 6 thereby detaching (or unlocking) the plate holder 40 from the implanted bone plate 6. Thereafter, the plate holder 40 is removed from the patient P through the incision, and the incision I is closed in a conventional manner.

There is a plurality of advantages arising from the various features of each of the embodiments of the assembly described herein. It will be noted that alternative embodiments of the assembly may not include all of the features described yet still benefit from at least some of the advantages of such features. Those of ordinary skill in the art may readily devise their own implementations of the assembly that incorporates one or more of the features and fall within the spirit and scope of the present invention as defined by the appended claims.

What is claimed is:

1. An assembly, comprising:
a guide component including:
a base defining a distal bone contacting surface and an opposite proximal surface and having (i) a coupling structure including a passageway sidewall that defines a first passageway and a first coupling component, said passageway sidewall defining a lateral passageway opening, and (ii) a finger extending from said first coupling structure, said finger defining a slot having a slot sidewall that defines a lateral slot opening that is common with respect to said lateral passageway opening so that said slot communicates with said first passageway through said passageway sidewall and said slot sidewall, and said coupling structure and said finger collectively defining said distal bone contacting surface of said base, and
a handle extending from said base; and
a sheath having (i) a proximal sheath end portion defining a proximal sheath opening, and (ii) a distal sheath end portion defining a distal sheath opening, said sheath defining a second passageway extending between said proximal sheath opening and said distal sheath opening, and said distal sheath end portion including a second coupling component configured to cooperate with said first coupling component to couple said sheath to said base, wherein said first passageway is aligned with said second passageway when said sheath is coupled to said base;
a stop structure extending through said proximal sheath opening and defining a central passage, said stop structure including an external surface having a plurality of keyways defined therein,
wherein said proximal sheath end portion includes a key member configured to be selectively received in any one of said plurality of keyways, and
wherein said stop structure is fixed in relation to said sheath when said key member is positioned in any one of said plurality of keyways.

2. The assembly of claim 1, wherein said central passage of said stop structure is aligned with said second passageway of said sheath, when said key member is positioned in any one of said plurality of keyways.

3. The assembly of claim 2, wherein said plurality of keyways is aligned in a row lengthwise of said stop structure.

4. The assembly of claim 3, wherein:
the stop structure further includes a plurality of indicia marks, and
the plurality of indicia marks are respectively positioned in association with said plurality of keyways.

5. The assembly of claim 3, wherein:
said second passageway of said sheath defines an axis,
said stop structure further includes a first flat exterior surface portion extending lengthwise of said stop structure, and said stop structure is axially movable in relation to said sheath when both (i) said stop structure is at least partially received within said second passageway of said sheath, and (ii) said key member of said sheath is aligned with said first flat exterior surface portion of said stop structure.

6. The assembly of claim 5, wherein:
said stop structure further includes a distal stop structure portion having a second flat exterior surface,
said second flat exterior surface portion is circumferentially offset from said first flat exterior portion.

7. The assembly of claim 2, further comprising a drill configured to be received within said central passage of said stop structure, wherein:
said drill includes (i) a distal drill portion having a first cutting surface, and (ii) a proximal drill portion having a first shoulder, and
said first shoulder contacts said stop structure to prevent further advancement of said drill through said central passage of said stop structure when said drill is received within said central passage of said stop structure.

8. The assembly of claim 7, further comprising a tap configured to be received within said central passage of said stop structure, wherein:
said tap includes (i) a distal tap portion having a second cutting surface, and (ii) a proximal tap portion having a second shoulder, and
said second shoulder contacts said stop structure to prevent further advancement of said tap through said central passage of said stop structure when said tap is received within said central passage of said stop structure.

9. The assembly of claim 1, wherein:
said first coupling component includes a set of internal threads defined by said passageway sidewall,
said second coupling component includes a set of external threads defined by an external surface of said first sheath, and
said set of internal threads are configured to mate with said set of external threads.

10. The assembly of claim 1, wherein said first coupling component is located within said first passageway.

11. The assembly of claim 1, wherein:
said passageway sidewall further defines a proximal passageway opening and a distal passageway opening, and
said first lateral opening extends from said proximal passageway opening to said distal passageway opening.

12. The assembly of claim 11, wherein:
said slot sidewall further defines a proximal slot opening and a distal slot opening, and
said second lateral opening extends from said proximal slot opening to said distal slot opening.

13. An assembly, comprising:
a guide component including:
a base defining a distal bone contacting surface and an opposite proximal surface and having (i) a coupling structure including a passageway sidewall that defines a first passageway and a first coupling component, said passageway sidewall defining a lateral passageway opening, and (ii) a finger extending from said first coupling structure, said finger defining a slot having a slot sidewall that defines a lateral slot opening that is common with respect to said lateral passageway opening so that said slot communicates with said first passageway through said passageway sidewall and said slot sidewall, and said coupling structure and said finger collectively defining said distal bone contacting surface of said base; and
a handle extending from said base; and
a first sheath having (i) a proximal sheath end portion defining a proximal sheath opening, and (ii) a distal sheath end portion defining a distal sheath opening, said first sheath defining a second passageway extending between said proximal sheath opening and said distal sheath opening, and said distal sheath end portion including a second coupling component configured to cooperate with said first coupling component to couple said first sheath to said base, and said first passageway being aligned with said second passageway when said first sheath is coupled to said base;
a second sheath defining a third passageway, said second sheath being positionable within said second passageway of said first sheath;
a guide wire positionable within said third passageway of said second sheath;
a stop structure defining a central passage, said stop structure including an external surface having a plurality of keyways defined therein, wherein (i) said proximal sheath end portion includes a key member configured to be selectively received in any one of said plurality of keyways, and (ii) said stop structure is fixed in relation to said first sheath when said key member is positioned in any one of said plurality of keyways; and
a drill configured to be received within said central passage of said stop structure when said stop structure is received within said second passageway of said first sheath, wherein (i) said drill includes a first distal portion having a first cutting surface, and a first proximal portion having a first shoulder, and (ii) said first shoulder contacts said stop structure to prevent further advancement of said drill through said central passage of said stop structure when said drill is received within said central passage of said stop structure.

14. The assembly of claim 13, further comprising:
a tap configured to be received within said central passage of said stop structure when said stop structure is received within said second passageway of said first sheath, wherein (i) said tap includes a second distal portion having a second cutting surface, and a second proximal portion having a second shoulder, and (ii) said second shoulder contacts said stop structure to prevent further advancement of said tap through said central passage of said stop structure when said tap is received within said central passage of said stop structure.

15. The assembly of claim 13, wherein:
said first coupling component includes a set of internal threads defined by said passageway sidewall,
said second coupling component includes a set of external threads defined by an external surface of said first sheath, and
said set of internal threads are configured to mate with said set of external threads.

16. The assembly of claim 13, wherein said first coupling component is located within said first passageway.

17. The assembly of claim 13, wherein:
said passageway sidewall further defines a proximal passageway opening and a distal passageway opening, and
said first lateral opening extends from said proximal passageway opening to said distal passageway opening.

18. The assembly of claim 17, wherein:
said slot sidewall further defines a proximal slot opening and a distal slot opening, and
said second lateral opening extends from said proximal slot opening to said distal slot opening.

19. An assembly, comprising:
a guide component including:
   a base defining a distal bone contacting surface and an opposite proximal surface and having (i) a coupling structure including a passageway sidewall that defines a first passageway and a first coupling component, said passageway sidewall defining a proximal passageway opening, a distal passageway opening, and a lateral passageway opening extending between said proximal passageway opening and said distal passageway opening, and (ii) a finger extending from said first coupling structure, said finger defining a slot having a slot sidewall that defines a proximal slot opening, a distal slot opening, and a lateral slot opening extending between said proximal slot opening and said distal slot opening, wherein said lateral slot opening is common with respect to said lateral passageway opening so that said slot communicates with said first passageway through said passageway sidewall and said slot sidewall, and wherein said coupling structure and said finger collectively defining said distal bone contacting surface of said base, and
   a handle extending from said base; and
a sheath having (i) a proximal sheath end portion defining a proximal sheath opening, and (ii) a distal sheath end portion defining a distal sheath opening, said sheath defining a second passageway extending between said proximal sheath opening and said distal sheath opening, and said distal sheath end portion including a second coupling component configured to cooperate with said first coupling component to couple said sheath to said base, wherein said first passageway is aligned with said second passageway when said sheath is coupled to said base.

20. The assembly of claim 19, wherein:
   said first coupling component includes a set of internal threads defined by said passageway sidewall,
   said second coupling component includes a set of external threads defined by an external surface of said first sheath, and
   said set of internal threads are configured to mate with said set of external threads.

21. The assembly of claim 19, wherein said first coupling component is located within said first passageway.

22. The assembly of claim 19, further comprising a stop structure extending through said proximal sheath opening and defining a central passage that is aligned with said second passageway of said sheath.

23. The assembly of claim 22, further comprising:
   a drill configured to be received within said central passage of said stop structure, wherein said drill includes (i) a distal drill portion having a first cutting surface, and (ii) a proximal drill portion having a first shoulder, and wherein said first shoulder contacts said stop structure to prevent further advancement of said drill through said central passage of said stop structure when said drill is received within said central passage of said stop structure; and
   a tap configured to be received within said central passage of said stop structure, wherein said tap includes (i) a distal tap portion having a second cutting surface, and (ii) a proximal tap portion having a second shoulder, and wherein said second shoulder contacts said stop structure to prevent further advancement of said tap through said central passage of said stop structure when said tap is received within said central passage of said stop structure.

* * * * *

UNITED STATES PATENT AND TRADEMARK OFFICE
CERTIFICATE OF CORRECTION

PATENT NO. : 8,808,300 B2  
APPLICATION NO. : 11/904520  
DATED : August 19, 2014  
INVENTOR(S) : Matthew V. Leyden et al.

Page 1 of 1

It is certified that error appears in the above-identified patent and that said Letters Patent is hereby corrected as shown below:

In the Specification

Col. 1, Line 44: Delete "3,554,193,and" and insert --3,554,193, and--
Col. 7, Line 43: Delete "316" and insert --312--
Col. 8, Line 36: Delete "328" and insert --327--
Col. 8, Line 51: Delete "310" and insert --306--
Col. 9, Line 31: Delete ""110,","" and insert --"110",--
Col. 10, Line 48: Delete "50" and insert --48--
Col. 11, Line 4: After "coupling", insert --component--
Col. 11, Line 18: Delete "44" and insert --46--
Col. 12, Line 59: Delete "passage" and insert --cavity--
Col. 14, Line 8: Delete "50" and insert --48--
Col. 14, Line 10: Delete "50" and insert --48--

Signed and Sealed this
Thirty-first Day of March, 2015

Michelle K. Lee
*Director of the United States Patent and Trademark Office*